US009717772B2

(12) United States Patent
Russ et al.

(10) Patent No.: US 9,717,772 B2
(45) Date of Patent: Aug. 1, 2017

(54) INTERVAL THERAPY FOR THE TREATMENT OF LOSS OF EYESIGHT IN HUMANS WITH GLAUCOMA AND OTHER DEGENERATIVE EYE DISEASES

(71) Applicant: Ramot at Tel-Aviv University Ltd., Tel-Aviv (IL)

(72) Inventors: Hermann Russ, Frankfurt am Main (DE); Wojciech Danysz, Nidderau (DE); Christopher Graham Raphael Parsons, Nidderau-Windecken (DE)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 14/410,200

(22) PCT Filed: Jun. 20, 2013

(86) PCT No.: PCT/EP2013/001832
§ 371 (c)(1),
(2) Date: Dec. 22, 2014

(87) PCT Pub. No.: WO2013/189606
PCT Pub. Date: Dec. 27, 2013

(65) Prior Publication Data
US 2016/0038558 A1 Feb. 11, 2016

Related U.S. Application Data

(60) Provisional application No. 61/661,971, filed on Jun. 20, 2012.

(30) Foreign Application Priority Data

Jun. 20, 2012 (EP) .................... 12004638

(51) Int. Cl.
*C07K 5/00* (2006.01)
*C07K 5/06* (2006.01)
*A61K 38/05* (2006.01)
*A61K 38/04* (2006.01)
*A61K 45/06* (2006.01)

(52) U.S. Cl.
CPC ............. *A61K 38/05* (2013.01); *A61K 45/06* (2013.01)

(58) Field of Classification Search
None
See application file for complete search history.

(56) References Cited

U.S. PATENT DOCUMENTS

| 7,781,396 B2 | 8/2010 | Gazit |
| 2005/0119187 A1 | 6/2005 | Hammer et al. |
| 2006/0148905 A1 | 7/2006 | Kim et al. |
| 2010/0093648 A1 | 4/2010 | Cruz |
| 2010/0143444 A1* | 6/2010 | Anantharamaiah .. A61K 9/0019 424/429 |
| 2011/0200531 A1 | 8/2011 | Tan |

FOREIGN PATENT DOCUMENTS

| JP | 2007-537699 | 12/2007 |
| JP | 2010-535728 | 11/2010 |
| WO | WO 00/47193 | 8/2000 |
| WO | WO 2005/000193 | 1/2005 |
| WO | WO 2008/148564 | 12/2008 |
| WO | WO 2009/024346 | 2/2009 |
| WO | WO 2012/055945 | 5/2012 |
| WO | WO 2012/066549 | 5/2012 |
| WO | WO 2013/189606 | 12/2013 |

OTHER PUBLICATIONS

International Preliminary Report on Patentability Dated Dec. 31, 2014 From the International Bureau of WIPO Re. Application No. PCT/EP2013/001832.
International Search Report and the Written Opinion Dated May 15, 2014 From the International Searching Authority Re. Application No. PCT/EP2013/001832.
Fradinger et al. "C-Terminal Peptides Coassemble Into A[Beta]42 Oligomers and Protect Neurons Against A[Beta]42-Induced Neurotoxicity", Proc. Natl. Acad. Sci. USA, PNAS, XP002723831, 105(37: 14175-14180, Sep. 16, 2008.
Frydman-Marom et al. "Cognitive-Performance Recovery of Alzheimer's Disease Model Mice by Modulation of Early Soluble Amyloidal Assemblies", Angewandte Chemie, International Edition, XP002601658, 48(11): 1981-1986, Jan. 1, 2009. p. 2016, 1-h col., Para 2.
Guo et al. "Targeting Amyloid-Beta in Glaucoma Treatment", Proc. Natl. Acad. Sci. USA, PNAS, XP002471873, 104(33): 13444-13449, Aug. 14, 2007.
Ladiwala et al. "Aromatic Small Molecules Remodel Toxic Soluble Oligomers of Amyloid Beta Through Three Independent Pathways", The Journal of Biological Chemistry, XP002723828, 286(5): 3209-3218, Feb. 4, 2011.
Ladiwala et al. "Resveratrol Selectively Remodels Soluble Oligomers and Fibrils of Amyloid A[Beta] Into Off-Pathway Conformers", the journal of Biological Chemistry, XP002723829, 285(31): 24228-24237, Jul. 30, 2010.
Luna et al. "Resveratrol Prevents the Expression of Glaucoma Markers Induced by Chronic Oxidative Stress in Trabecular Meshwork Cells", Food and Chemical Toxicology, XP025769233, 47(1): 198-204, Jan. 1, 2009.
McLaurin et al. "Inositol Stereoisomers Stabilize an Oligomeric Aggregate of Alzheimer Amyloid Beta Peptide and Inhibit A[Beta]-Induced Toxicity", the Journal of Biological Chemistry, XP003010970, 275(24): 18495-18502, Jun. 16, 2000.
Rigacci et al. "A[Beta](1-42) Aggregates Into Non-Toxic Amyloid Assemblies in the Presence of the Natural Polyphenol Oleuropein Aglycon", Current Alzheimer Research, XP009177758, 8(8): 841-852, Dec. 2011.

(Continued)

Primary Examiner — Satyanarayana R Gudibande

(57) ABSTRACT

Methods for the prevention and treatment of ocular disorders, in particular glaucoma, through blocking the toxic effects of β-amyloid (Aβ) derivatives, pharmaceutical compositions for effecting such prevention and interval treatment thereof.

15 Claims, 2 Drawing Sheets

(56) References Cited

OTHER PUBLICATIONS

Sheu et al. "Resveratrol Protects Human Retinal Pigment Epithelial Cells From Acrolein-Induced Damage", Journal of Ocular Pharmacology and Therapeutics, XP002723830, 26(3): 231-236, Jun. 2010.
Yun et al. "Paradoxical Strategy for Treating Chronic Diseases Where the Therapeutic Effect Is Derived From Compensatory Response Rather Than Drug Effect", Medical Hypotheses, XP004952012, 64(5): 1050-1059, Jan. 1, 2005. p. 1052, 1-h Col., Lines 24-27, p. 1053, r-h Col., Lines 3-12.
Zhang et al. "Epigallocatechin Gallate, An Active Ingredient From Green Tea, Attenuates Damaging Influences to the Retina Caused by Ischemia/Reperfusion", Brain Research, XP022156863, 1159: 40-53, Available Online May 26, 2007.
Notice of Reason for Rejection Dated Feb. 28, 2017 From the Japan Patent Office Re. Application No. 2015-517634. (4 Pages).
Translation of Notice of Reason for Rejection Dated Feb. 28, 2017 From the Japan Patent Office Re. Application No. 2015-517634. (9 Pages).
Frydman-Marom et al. "The General Amyloid Formation Inhibition Effect of a Designed Small Aromatic Beta-Breaking Peptide", Amyloid, 18(3): 119-127, Sep. 2011.
Sun et al. "A Survey of Peptides With Effective Therapeutic Potential in Alzheimer's Disease Rodent Models or in Human Clinical Studies", Mini-Reviews in Medicinal Chemistry, 12(5): 388-398, May 2012.

\* cited by examiner

INTERVAL THERAPY FOR THE TREATMENT OF LOSS OF EYESIGHT IN HUMANS WITH GLAUCOMA AND OTHER DEGENERATIVE EYE DISEASES

RELATED APPLICATIONS

This application is a National Phase of PCT Patent Application No. PCT/EP2013/001832 having International filing date of Jun. 20, 2013, which claims the benefit of priority of European Patent Application No. 12004638.8 filed on Jun. 20, 2012, and which also claims the benefit of priority under 35 USC §119(e) of U.S. Provisional Patent Application No. 61/661,971 filed on Jun. 20, 2012. The contents of the above applications are all incorporated by reference as if fully set forth herein in their entirety.

SEQUENCE LISTING STATEMENT

The ASCII file, entitled 61148SequenceListing.txt, created on Dec. 21, 2014, comprising 8,710 bytes, submitted concurrently with the filing of this application is incorporated herein by reference.

FIELD OF THE INVENTION

The present invention is concerned with methods for the prevention and treatment of ocular disorders, in particular glaucoma and macular degeneration, through modulating the toxic effects of β-amyloid (Aβ) derivatives, pharmaceutical compositions for effecting such prevention and treatment thereof, and specific administration effective for such treatment.

BACKGROUND OF THE INVENTION

Studies have shown that glaucoma is the second leading cause of blindness in the United States [Leske M C. The epidemiology of open-angle glaucoma: a review. Am J Epidemiology 1983; 118: 166-191]. The pathologic correlate of glaucoma is the progressive degeneration of retinal ganglion cells (RGC) and their axons which form the optic nerve.

The classification of glaucoma includes the following different types: primary angle-closure glaucoma, secondary open-angle glaucoma, steroid-induced glaucoma, traumatic glaucoma, pigmentary dispersion syndrome, pseudoexfoliation syndrome, secondary angle-closure glaucoma, neovascular glaucoma, uveitis and glaucoma and other non further specified eye pathologies.

Similarly, macular degeneration is a condition involving a pathology of the retina which has also been attributed to the occurrence of β-amyloid and leads to a progressive loss of vision, leading finally to blindness.

In the past, the definition of glaucoma included an elevation in the intraocular pressure (IOP) over a normal range. However, many individuals with clearly elevated IOP do not develop glaucoma, and up to 50% of patients with glaucoma do not have an increased IOP.

Currently available medications for the treatment of glaucoma belong to several pharmacological classes, including β-adrenergic blockers, cholinergic agonists, carbonic anhydrase inhibitors, and alpha2 agonists. All operate under a mechanism whereby the IOP is lowered. These existing therapies are typically administered as eye drops. Hyperosmotics may be administered intravenously for emergency treatment. In addition, laser therapy and surgical approaches are applied in special cases.

Irrespective of therapy, after 20 years of follow-up in glaucoma patients, glaucoma-related blindness will have reached 27% in at least one eye and 9% in both eyes [Hattenhauer M G, Johnson D H, Ing H H, et al. The probability of blindness from open-angle glaucoma. Ophthalmology 1998; 105: 2099-2104]. Thus, there exists a significant unmet medical need for alternative treatment strategies. Particularly for patients with progressive glaucomatous damage under normalized IOP, a therapy focusing on degenerating retinal ganglion cells is needed.

There are different theories regarding the cause for the degeneration of the retinal ganglion cells including mechanical, vascular and excitotoxic mechanisms. Only recently, β-amyloid (Aβ) has been found to co-localize with dying retinal ganglion cells [McKinnon S J. Glaucoma: Ocular Alzheimer's disease? Front Biosci. 2003; 8: 1140-1156; Yoneda S, Hara H, Hirata A, Fukushima M, Inomata Y, Tanihara H. Vitreous fluid levels of beta-amyloid(1-42) and tau in patients with retinal diseases. Jpn J Ophthalmol. 2005; 49(2): 106-108]. Animal studies demonstrate that, particularly, the soluble $A\beta_{1-42}$ peptide oligomers are very potent toxins for retinal ganglion cells [Dahlgren K N, Manelli A M, Stine W B Jr, Baker L K, Krafft G A, LaDu M J. Oligomeric and fibrillar species of amyloid-beta peptides differentially affect neuronal viability. J Biol Chem. 2002; 277(35): 32046-32053; Guo L, Salt T E, Luong V, Wood N, Cheung W, Maass A, Ferrari G, Russo-Marie F, Sillito A M, Cheetham M E, Moss S E, Fitzke F W, Cordeiro F. Targeting amyloid-β in glaucoma treatment. PNAS 2007; 104 (33): 13444-13449].

Multiple potential treatments targeting Aβ are under development. The common mechanism of these approaches is to counteract the detrimental effects of Aβ, either by preventing its formation (e.g. APP secretase inhibitors), by neutralizing Aβ through antibodies, or by interfering with Aβ aggregation. The latter mechanism is of increasing interest within the scientific community since data from animal models clearly show beneficial effects of Aβ aggregation inhibitors or Aβ aggregation modulators on Aβ-induced neurotoxicity.

Inhibition of neurotoxic Aβ aggregation species has been shown to reduce glaucomatous degeneration of retinal ganglion cells [Guo, et al., PANS 2007, 13444]. The inhibitors used in these animal experiments were Congo red and Aβ antibodies. These agents are pharmacological research tools only and are not appropriate for treatment of humans for various reasons.

It would be an advantage to provide novel methods for the prevention and treatment of ocular disorders, in particular glaucoma and macular degeneration, and pharmaceutical compositions for effecting such prevention and treatment thereof. According to the current scientific understanding, Aβ aggregation inhibitors or Aβ aggregation modulators are administered continuously over long periods of time to cause a therapeutically relevant neuroprotective effect. Interruption of the therapy—even for a short period only—is understood to lead to the situation that, in the absence of the inhibitor/modulator, neurotoxic aggregation immediately restarts and the disease progresses (potentially even more aggressively then before). The same paradigm is postulated for the therapy of other Aβ-associated diseases as mentioned above.

Moreover, treatment of Aβ-associated eye conditions, such as glaucoma or macular degeneration, often requires dosage routes involving uncomfortable steps, such as intravitreal injections. Accordingly, there is a need to improve patient compliance and general wellbeing.

It would be a clear advantage for patients if the neuroprotective effects could be achieved by an interval therapy characterized by a first effective dose followed by "booster" doses with the possibility of drug-free periods in between, rather than by a strictly continuous dosage regimen. Of course, such an dosage schedule should nonetheless also ensure the best possible clinical outcome of therapy.

PCT International Application No. PCT/EP2008/006888 discloses that Aβ aggregation modulators may produce a therapeutically relevant neuroprotective effect in the treatment of glaucoma.

With the instant invention, it has been discovered that interval therapy employing such Aβ aggregation modulators may be an effective approach for the treatment of glaucoma and macular degeneration.

Moreover, it has been determined that intervallic treatment may prevent recurrence of glaucoma in patients with sufficient or stable treatment effects through administering a reduced dose of an Aβ aggregation modulator. A benefit associated with such treatment is a significantly reduced drug exposure, in particular reduced chronic exposure while the therapeutic effect is still sufficient. Also, it increases convenience of dosage for patients and thereby positively influences compliance.

Additional needs in the art which are addressed by the invention will become apparent hereinafter, and still further needs will be apparent to one skilled in the art.

SUMMARY OF THE INVENTION

What we therefore believe to be comprised by our invention may be summarized inter alia in the following words:

A method for the prevention and/or treatment of at least one optical condition associated with β-amyloid (Aβ) toxicity in a subject in need thereof, comprising the step of administering to the subject a peptide comprising an amino acid sequence X-Y or Y-X, wherein X is an aromatic amino acid and Y is an additional amino acid other than glycine, which peptide is administered daily for a first period of at least one (1) day in at least a therapeutically effective dose, followed by a second period of at least one (1) week
  a) wherein the peptide is not administered, or
  b) wherein the peptide is administered at a dose which is more than 0% and up to 75% of the therapeutically effective dose,
whereafter the method of administration may be repeated;

Such a method, wherein during the second period the peptide is administered at a dose which is 20-75% of the therapeutically effective dose;

Such a method, wherein during the second period the peptide is administered at a dose which is 25-50% of the therapeutically effective dose;

Such a method, wherein during the second period the peptide is not administered followed by further first period of administration to the subject of a therapeutically effective dose of the peptide;

Such a method, wherein the second period is followed by further first period of administration to the subject of a therapeutically effective dose of the peptide;

Such a method, wherein the administration of the therapeutically effective dose of the peptide during the first period is continued for at least one week;

Such a method, wherein the administration of the therapeutically effective dose of the peptide during the first period is continued for at most one month;

Such a method, wherein the second period is at least one (1) month, or at least 2 months;

Such a method, wherein the second period is at most 3 months, or at most 6 months, or at most 1 year;

Such a method, wherein the second period is from three (3) to six (6) months;

Such a method, wherein the peptide is selected from D-Trp-Aib (SEQ ID NO. 30), Tyr-Tyr (SEQ ID NO. 6), Tyr-Tyr-NH2 (SEQ ID NO. 11), D-Tyr-Aib (SEQ ID NO. 16), D-Pro-D-Tyr (SEQ ID NO. 17), D-Tyr-D-Pro (SEQ ID NO. 18), D-Tyr-D-Tyr (SEQ ID NO. 27), D-Pro-Aib (SEQ ID NO. 28), D-Phe-D-Pro (SEQ ID NO. 29), D-Trp-D-Pro (SEQ ID NO. 31), D-Phe-Pro (SEQ ID NO. 32), and Pro-D-Phe (SEQ ID NO. 33);

Such a method, wherein the peptide is in the form of a pharmaceutically acceptable salt;

Such a method, wherein the peptide or pharmaceutically acceptable salt thereof is administered in the form of several single doses administered within a period of time consisting of one (1) or more days;

Such a method, wherein the peptide or pharmaceutically acceptable salt thereof is administered at different dose strengths selected from up and down titration;

Such a method, wherein the peptide or pharmaceutically acceptable salt thereof is administered in an immediate release formulation;

Such a method, wherein the peptide or pharmaceutically acceptable salt thereof is administered in a modified release formulation;

Such a method, wherein the at least one optical condition is selected from the group consisting of primary angle-closure glaucoma, secondary open-angle glaucoma, wide-angle glaucoma, steroid-induced glaucoma, traumatic glaucoma, pigmentary dispersion syndrome, pseudo exfoliation syndrome, secondary angle-closure glaucoma, neovascular glaucoma, uveitis and glaucoma, age-related macular degeneration, diabetic retinopathy, degenerative optic neuropathy and eye pathologies characterized by a progressive loss of vision leading finally to blindness;

Such a method, wherein the peptide is administered in combination in both the first and/or second periods with a therapeutically effective dose of at least one additional pharmaceutical agent which is effective in treating or preventing at least one optical condition;

Such a method, wherein the at least one additional pharmaceutical agent is a medication administered to treat eye diseases and contains at least one agent selected from anti-glaucoma drugs, antibiotics, anti-inflammatory drugs, steroids, anti-allergic drugs and artificial tear fluid;

Such a method, wherein the at least one additional pharmaceutical agent is selected from acetazolamide, diclofenamide, carteolol, timolol, metipranolol, betaxolol, pindolol, levobunolol, brimonidine, clonidine, pilocarpine, carbachol, dipivefrine, apraclonidine, brinzolamide, dorzolaminde, bimatoprost, travaprost, latanoprost, chlortetracycline, ciprofloxacine, ofloxacine, fusidinic acid, gentamicine, kanamycine, levofloxacine, lomefloxacine, oxytetracycline, natamycine, azidamfenicole, chloramphenicole, tobramycine, erythromycine, polymyxin-B, acaclovir, trifluridine, betamethasone, dexamethasone, fluorometholone, hydrocortisone, prednisolone, rimexolone, cromoglicate, azelastine, lodoxamide, emedastine, nedocromile, levocabastine, olopatadinea, ketotifene, hypromellose, carbomere, hyaluronate, carmellose, hypromellose, povidone, hyetellose, polivinylalcohole, dexpanthenole, tetryzoline, troxerutine, tramazoline, naphazoline, xylometazoline, phenylephrine and antazoline;

Such a method, for the prevention and/or treatment of at least one optical condition associated with β-amyloid (Aβ) toxicity in a subject in need thereof, comprising the step of administering to the subject a substance and/or combination thereof selected from (−)-epigallocatechin-3-gallate (EGCG), D-pep (QSHYRHISPAQV), IAPP-GI, mannose, sucrose, raffinose, resveratrol, phloretin, naringenin, apigenin, quercetin, taiwaniaflavone (TF), 2',8"-biapigenin, amentoflavone, and sumaflavone, which substance and/or combination thereof is/are administered daily for a first period of at least one (1) day in at least a therapeutically effective dose, followed by a second period of at least one (1) week
- a) wherein the substance is not administered or
- b) wherein the substance is administered at a dose which is more than 0% and up to 75% of the therapeutically effective dose, whereafter the method of administration may be repeated;

Such a method, for the prevention and/or treatment of at least one optical condition associated with β-amyloid (Aβ) toxicity in a subject in need thereof, comprising the step of administering to the subject a substance daily for a first period of at least one (1) day in at least a therapeutically effective dose, followed by a second period of at least one (1) week
- a) wherein the substance is not administered or
- b) wherein the substance is administered at a dose which is more than 0% and up to 75% of the therapeutically effective dose, whereafter the method of administration may be repeated; wherein the substance is selected from the group consisting of:

(R)-(tert-butyl 2-(2-amino-3-(1H-indol-3-yl)propanamido)-2-methylpropanoate),
(methyl 2-(2-amino-3-(1H-indol-3-yl)-2-methylpropanamido)-2-methylpropanoate),
(methyl 1-(2-amino-3-(1H-indol-3-yl)-2-methylpropanamido)cyclopentanecarboxylate),
(R)-1-(2-amino-3-(1H-indol-3-yl)propanamido)cyclopentanecarboxylic acid,
(R)-(1-(2-amino-3-(1H-indol-3-yl)propanamido)cyclopropanecarboxylic acid),
(ethyl 1-(2-amino-3-(1H-indol-3-yl)propanamido)cyclopropanecarboxylate),
1-(2-amino-3-(1H-indol-3-yl)propanamido)cyclohexane carboxylic acid,
ethyl 1-(2-amino-3-(1H-indol-3-yl)propanamido)cyclohexane carboxylate,
methyl 1-(2-amino-3-(1H-indol-3-yl)propanoyl)-2-methylpyrrolidine-2-carboxylate,
(R)-3-(2-amino-3-(1H-indol-3-yl)propanamido)oxetane-3-carboxylic acid,
(R)-3-(2-amino-3-(1H-indol-3-yl)propanamido)oxetane-3-carboxamide,
(R)-2-amino-N-1(1-amino-2-methyl-1-oxopropan-2-yl)-3-(1-H-indol-3-yl)propanamide
(R)-3-((2-amino-3-(1H-indol-3-yl)-2,2-dimethyl-hex-3-enoic acid;

Such a method, for the prevention and/or treatment of at least one optical condition associated with β-amyloid (Aβ) toxicity in a subject in need thereof, comprising the step of administering to the subject a substance daily for a first period of at least one (1) day in at least a therapeutically effective dose, followed by a second period of at least one (1) week
- a) wherein the substance is not administered or
- b) wherein the substance is administered at a dose which is more than 0% and up to 75% of the therapeutically effective dose, whereafter the method of administration may be repeated; wherein the substance is selected from the group consisting of N—((R)-2-Amino-3-(1H-indol-3-yl)-propyl)-2,2-dimethylmalonamic acid,
(E)-(R)-5-Amino-6-(1H-indol-3-yl)-2,2-dimethyl-hex-3-enoic-acid,
(E)-(R)-5-Amino-6-(1H-indol-3-yl)-2,2-dimethyl-hex-3-enoic acid amide,
(E)-(R)-5-Amino-6-(1H-indol-3-yl)-2,2-dimethyl-hex-3-enoic-acid-methylamide,
(E)-(R)-5-Acetylamino-6-(1H-indol-3-yl)-2,2-dimethyl-hex-3-enoic-acid,
(R)-5-Amino-6-(1H-indol-3-yl)-2,2-dimethyl-4-oxo-hexanoic-acid,
(R)-5-Amino-4-hydroxy-6-(1H-indol-3-yl)-2,2-dimethyl-hexanoic-acid,
(R,E)-6-(1H-indol-3-yl)-2,2-dimethyl-5-(N-methylacetamide)hex-3-enoic acid,
(E)-(R)-5-Acetylamino-6-(1H-indol-3-yl)-2,2-dimethyl-hex-3-enoic-acid-amide,
(E)-(R)-5-Acetylamino-6-(1H-indol-3-yl)-2,2-dimethyl-hex-3-enoic-acid-methylamide,
(E)-(S)-5-Amino-6-(1H-indol-3-yl)-2,2-dimethyl-hex-3-enoic-acid-amide,
(E)-(S)-5-Amino-6-(1H-indol-3-yl)-2,2-dimethyl-hex-3-enoic-acid-methylamide,
(R)-5-Amino-6-(1H-indol-3-yl)-2,2-dimethyl-4-oxo-hexanoic-acid-methylamide,
(R)-5-Acetylamino-6-(1H-indol-3-yl)-2,2-dimethyl-4-oxo-hexanoic acid;

Further comprising bulky non-toxic β-amyloid (Aβ) protein aggregates for use in prevention and/or treatment at least one optical condition associated with Aβ toxicity in a subject in need thereof;

Such aggregates, wherein the aggregates are induced and sustained by means of interval therapy by administering to the subject an Aβ aggregation modulator, wherein the Aβ aggregation modulator is administered daily for a first period of at least one (1) day in at least a therapeutically effective dose, followed by a second period of at least one (1) week
- a) wherein the Aβ aggregation modulator is not administered or
- b) wherein the Aβ aggregation modulator is administered at a dose which is more than 0% and up to 75% of the therapeutically effective dose, whereafter the method of administration may be repeated; Such aggregates, wherein the aggregates are induced and/or sustained by administering to the subject an Aβ aggregation modulator selected from the group consisting of D-Trp-Aib (SEQ ID NO. 30), (E)-(R)-5-Amino-6-(1H-indol-3-yl)-2,2-dimethyl-hex-3-enoic-acid, (R)-2-amino-N-1 (1-amino-2-methyl-1-oxopropan-2-yl)-3-(1-H-indol-3-yl) propanamide and (R)-3-((2-amino-3-(1H-indol-3-yl)-2,2-dimethyl-hex-3-enoic acid, which Aβ aggregation modulator is administered daily for a first period of at least one (1) day in at least a therapeutically effective dose, followed by a second period of at least one (1) week
- a) wherein the Aβ aggregation modulator is not administered or b) wherein the Aβ aggregation modulator is administered at a dose which is more than 0% and up to 75% of the therapeutically effective dose, whereafter the method of administration may be repeated;

Such aggregates, wherein the aggregates are induced in a conditioned medium of Aβ producing cells or from synthetic Aβ, wherein an Aβ aggregation modulator selected from the group consisting of D-Trp-Aib (SEQ ID NO. 30), (E)-(R)-5-Amino-6-(1H-indol-3-yl)-2,2-dimethyl-hex-3-enoic-acid, (R)-2-amino-N-1(1-amino-2-methyl-1-oxopropan-2-yl)-3-(1-H-indol-3-yl)propanamide and (R)-3-((2-amino-3-(1H-indol-3-yl)-2,2-dimethyl-hex-3-enoic acid, has been added to the conditioned medium of Aβ producing cells or to the synthetic Aβ under conditions adequate for inducing aggregation into bulky non-toxic aggregates, whereafter such aggregates are isolated and washed.

The invention also relates to a peptide comprising an amino acid sequence X-Y or Y-X, wherein X is an aromatic amino acid and Y is an additional amino acid other than glycine for use in the prevention and/or treatment of at least one optical condition associated with β-amyloid (Aβ) toxicity in a subject in need thereof, which peptide is administered daily for a first period of at least one (1) day in at least a therapeutically effective dose, followed by a second period of at least one (1) week a) wherein the peptide is not administered, or b) wherein the peptide is administered at a dose which is more than 0% and up to 75% of the therapeutically effective dose, whereafter the method of administration may be repeated;

Such peptide, wherein during the second period the peptide is administered at a dose which is 20-75% of the therapeutically effective dose;

Such peptide, wherein during the second period the peptide is administered at a dose which is 25-50% of the therapeutically effective dose;

Such peptide, wherein during the second period the peptide is not administered followed by further first period of administration to the subject of a therapeutically effective dose of the peptide;

Such peptide, wherein the second period is followed by further first period of administration to the subject of a therapeutically effective dose of the peptide;

Such peptide, wherein the administration of the therapeutically effective dose of the peptide during the first period is continued for at least one week;

Such peptide, wherein the administration of the therapeutically effective dose of the peptide during the first period is continued for at most one month;

Such peptide, wherein the second period is at least one (1) month, or at least 2 months;

Such peptide, wherein the second period is at most 3 months, or at most 6 months, or at most 1 year;

Such peptide, wherein the second period is from three (3) to six (6) months;

Such peptide, wherein the peptide is selected from D-Trp-Aib (SEQ ID NO. 30), Tyr-Tyr (SEQ ID NO. 6), Tyr-Tyr-NH2 (SEQ ID NO. 11), D-Tyr-Aib (SEQ ID NO. 16), D-Pro-D-Tyr (SEQ ID NO. 17), D-Tyr-D-Pro (SEQ ID NO. 18), D-Tyr-D-Tyr (SEQ ID NO. 27), D-Pro-Aib (SEQ ID NO. 28), D-Phe-D-Pro (SEQ ID NO. 29), D-Trp-D-Pro (SEQ ID NO. 31), D-Phe-Pro (SEQ ID NO. 32), and Pro-D-Phe (SEQ ID NO. 33);

Such peptide, wherein the peptide is in the form of a pharmaceutically acceptable salt;

Such peptide, wherein the peptide or pharmaceutically acceptable salt thereof is administered in the form of several single doses administered within a period of time consisting of one (1) or more days;

Such peptide, wherein the peptide or pharmaceutically acceptable salt thereof is administered at different dose strengths selected from up and down titration;

Such peptide, wherein the peptide or pharmaceutically acceptable salt thereof is administered in an immediate release formulation;

Such peptide, wherein the peptide or pharmaceutically acceptable salt thereof is administered in a modified release formulation;

Such peptide, wherein the at least one optical condition is selected from the group consisting of primary angle-closure glaucoma, secondary open-angle glaucoma, wide-angle glaucoma, steroid-induced glaucoma, traumatic glaucoma, pigmentary dispersion syndrome, pseudo exfoliation syndrome, secondary angle-closure glaucoma, neovascular glaucoma, uveitis and glaucoma, age-related macular degeneration, diabetic retinopathy, degenerative optic neuropathy and eye pathologies characterized by a progressive loss of vision leading finally to blindness;

Such peptide, wherein the peptide is administered in combination in both the first and/or second periods with a therapeutically effective dose of at least one additional pharmaceutical agent which is effective in treating or preventing at least one optical condition;

Such peptide, wherein the at least one additional pharmaceutical agent is a medication administered to treat eye diseases and contains at least one agent selected from anti-glaucoma drugs, antibiotics, anti-inflammatory drugs, steroids, anti-allergic drugs and artificial tear fluid;

Such peptide, wherein the at least one additional pharmaceutical agent is selected from acetazolamide, diclofenamide, carteolol, timolol, metipranolol, betaxolol, pindolol, levobunolol, brimonidine, clonidine, pilocarpine, carbachol, dipivefrine, apraclonidine, brinzolamide, dorzolaminde, bimatoprost, travaprost, latanoprost, chlortetracycline, ciprofloxacine, ofloxacine, fusidinic acid, gentamicine, kanamycine, levofloxacine, lomefloxacine, oxytetracycline, natamycine, azidamfenicole, chloramphenicole, tobramycine, erythromycine, polymyxin-B, acaclovir, trifluridine, betamethasone, dexamethasone, fluorometholone, hydrocortisone, prednisolone, rimexolone, cromoglicate, azelastine, lodoxamide, emedastine, nedocromile, levocabastine, olopatadinea, ketotifene, hypromellose, carbomere, hyaluronate, carmellose, hypromellose, povidone, hyetellose, polivinylalcohole, dexpanthenole, tetryzoline, troxerutine, tramazoline, naphazoline, xylometazoline, phenylephrine and antazoline;

The invention also relates to a substance and/or combination thereof selected from (−)-epigallocatechin-3-gallate (EGCG), D-pep (QSHYRHISPAQV), IAPP-GI, mannose, sucrose, raffinose, resveratrol, phloretin, naringenin, apigenin, quercetin, taiwaniaflavone (TF), 2',8"-biapigenin, amentoflavone, and sumaflavone for use in the prevention and/or treatment of at least one optical condition associated with β-amyloid (Aβ) toxicity in a subject in need thereof, which substance and/or combination thereof is/are administered daily for a first period of at least one (1) day in at least a therapeutically effective dose, followed by a second period of at least one (1) week a) wherein the substance is not administered or b) wherein the substance is administered at a dose which is more than 0% and up to 75% of the therapeutically effective dose, whereafter the method of administration may be repeated;

As well as a substance selected from the group consisting of:

(R)-(tert-butyl 2-(2-amino-3-(1H-indol-3-yl)propanamido)-2-methylpropanoate), (methyl2-(2-amino-3-(1H-indol-3-yl)-2-methylpropanamido)-2-methylpropanoate), (methyl 1-(2-amino-3-(1H-indol-3-yl)-2-ethylpropanamido)
cyclopentanecarboxylate),
(R)-1-(2-amino-3-(1H-indol-3-yl)propanamido)cyclopen-
tanecarboxylic acid,
(R)-(1-(2-amino-3-(1H-indol-3-yl)propanamido)cyclopro-
panecarboxylic acid),
(ethyl 1-(2-amino-3-(1H-indol-3-yl)propanamido)cyclopro-
panecarboxylate),
1-(2-amino-3-(1H-indol-3-yl)propanamido)cyclohexane
carboxylic acid,
ethyl 1-(2-amino-3-(1H-indol-3-yl)propanamido)cyclo-
hexane carboxylate,
methyl 1-(2-amino-3-(1H-indol-3-yl)propanoyl)-2-methyl-
pyrrolidine-2-carboxylate,
(R)-3-(2-amino-3-(1H-indol-3-yl)propanamido)oxetane-3-
carboxylic acid,
(R)-3-(2-amino-3-(1H-indol-3-yl)propanamido)oxetane-3-
carboxamide,
(R)-2-amino-N-1(1-amino-2-methyl-1-oxopropan-2-yl)-3-
(1-H-indol-3-yl)propanamide,
(R)-3-((2-amino-3-(1H-indol-3-yl)-2,2-dimethyl-hex-3-
enoic acid
for use in the prevention and/or treatment of at least one optical condition associated with β-amyloid (Aβ) toxicity in a subject in need thereof, which substance is administered to the subject daily for a first period of at least one (1) day in at least a therapeutically effective dose, followed by a second period of at least one (1) week
a) wherein the substance is not administered or
b) wherein the substance is administered at a dose which is more than 0% and up to 75% of the therapeutically effective dose,
whereafter the method of administration may be repeated;
And to a substance selected from the group consisting of:
N—((R)-2-Amino-3-(1H-indol-3-yl)-propyl)-2,2-dimethyl-malonamic acid, (E)-(R)-5-Amino-6-(1H-indol-3-yl)-2,2-dimethyl-hex-3-enoic-acid, (E)-(R)-5-Amino-6-(1H-indol-3-yl)-2,2-dimethyl-hex-3-enoic acid amide, (E)-(R)-5-Amino-6-(1H-indol-3-yl)-2,2-dimethyl-hex-3-enoic-acid-methylamide, (E)-(R)-5-Acetylamino-6-(1H-indol-3-yl)-2,2-dimethyl-hex-3-enoic-acid, (R)-5-Amino-6-(1H-indol-3-yl)-2,2-dimethyl-4-oxo-hexanoic-acid, (R)-5-Amino-4-hydroxy-6-(1H-indol-3-yl)-2,2-dimethyl-hexanoic-acid, (R,E)-6-(1H-indol-3-yl)-2,2-dimethyl-5-(N-methylacet-amide)hex-3-enoic acid, (E)-(R)-5-Acetylamino-6-(1H-indol-3-yl)-2,2-dimethyl-hex-3-enoic-acid-amide, (E)-(R)-5-Acetylamino-6-(1H-indol-3-yl)-2,2-dimethyl-hex-3-enoic-acid-ethylamide, (E)-(S)-5-Amino-6-(1H-indol-3-yl)-2,2-dimethyl-hex-3-enoic-acid-amide, (E)-(S)-5-Amino-6-(1H-indol-3-yl)-2,2-dimethyl-hex-3-enoic-acid-methylamide, (R)-5-Amino-6-(1H-indol-3-yl)-2,2-dimethyl-4-oxo-hexanoic-acid-methylamide, (R)-5-Acetylamino-6-(1H-indol-3-yl)-2,2-dimethyl-4-oxo-hexanoic acid
for use in the prevention and/or treatment of at least one optical condition associated with β-amyloid (Aβ) toxicity in a subject in need thereof, which substance is administering to the subject daily for a first period of at least one (1) day in at least a therapeutically effective dose, followed by a second period of at least one (1) week
a) wherein the substance is not administered or
b) wherein the substance is administered at a dose which is more than 0% and up to 75% of the therapeutically effective dose,
whereafter the method of administration may be repeated.

DETAILED DESCRIPTION OF THE INVENTION

Figure 1:
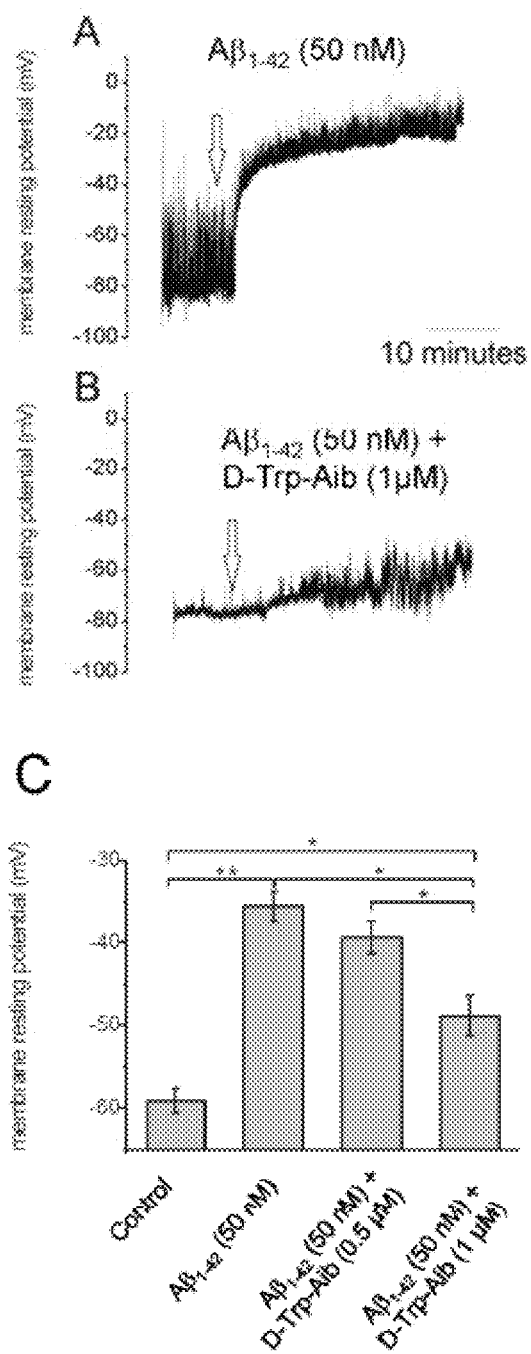
FIGS. 1A-C are graphs showing the neuroprotective effects of D-Trp-Aib tested on retinal ganglion cells.

"Interval treatment" as used herein refers to treatment wherein initially a first therapeutically effective dose is administered for a first period and a lower second dose, e.g. second dose being between 0 and 0.75 of the first dose, is administered for a defined second period.

With respect to the first therapeutically effective dose administration, such administration may also consist of several single doses (typically 1-10) administered within a short period of time (typically 1-7 days). Moreover, in the situation where several doses are administered, they may vary in their dosage strength. It is intended that such variation may include both up and down titration depending on the drug and its tolerability.

In particular with respect to treatment of optical conditions, the route of the first dose may be different from the route for the second dose. For example, the first dose may be administered via intravitreal injection and the second dose may be administered topically.

"Intermittent interval treatment" refers to specific embodiments of interval treatment wherein the second dose equals 0% of the first dose.

The second period will often be a longer time period than the first period. For example, the first period may be one day and the second period may be one or more weeks, or one or more months; or the first period will be one week and the second period will be two or more weeks, or one or more months. Often, the second period will be less than or equal to a year.

"Continuous treatment" as used herein does not comprise the above-defined application of the second dose for the second period of time.

The present invention addresses the limitations of conventional therapy for optical disorders and provides for a pharmaceutically acceptable therapy to effectively treat the loss of eyesight in humans with glaucoma and other degenerative ocular disorders. The underlying mechanism is a prevention or reversal of the loss of retinal ganglion cells through blocking the toxic effects of particular neurotoxic Aβ species.

Representative substances described for the instant therapy were initially designed for the treatment of diseases characterized by formation of amyloid fibrils, such as type II diabetes and prion diseases [Porat Y, Mazor Y, Efrat S, Gazit E. Inhibition of islet amyloid polypeptide fibril formation: A potential role for heteroaromatic interactions. Biochemistry 2004; 43:14454-14462], and degenerative diseases of the brain including Alzheimer's dementia [GAZIT, E., US Published Application No. US2006/0234947 A1]. More specifically, Gazit discloses that short chain peptides, possibly comprising modified amino acids such as aminoisobutyric acid, have application in the disruption of the formation of toxic Aβ species by interacting with molecular recognition processes and amyloid fibril self assembly. [Gazit, 2006] We have determined that these substances show therapeutic effects in another organ system distinct from the brain, i.e., the eyes. PCT International Application No. PCT/EP2008/006888. These substances demonstrate therapeutic effect in the prevention and treatment of retinal ganglion cell loss in animal models of glaucoma. Compared to known agents, Congo red and Aβ antibodies, these substances have the following advantages:

They are small molecules which can be produced cost-effectively in large scale.

They can easily be administered to patients, either orally (for instance as tablets or capsules), or locally (for instance eye drops, eye cream, intraocular depot).

They are well tolerated.

They have simple pharmacokinetic properties.

Yet additional substances may also find application in the methods of the instant invention. Specifically, the invention comprises methods utilizing the polyphenol (−)-epigallocatechin-3-gallate (EGCG) (Hudson S A, Ecroyd H, Dehle F C, Musgrave I F, Carver J A. (−)-epigallocatechin-3-gallate (EGCG) maintains kappacasein in its pre-fibrillar state without redirecting its aggregation pathway. J Mol Biol 2009 Sep. 25; 392(3):689-700) (Ehrnhoefer D E, Bieschke J, Boeddrich A, Herbst M, Masino L, Lurz R, et al. EGCG redirects amyloidogenic polypeptides into unstructured, off-pathway oligomers. Nat Struct Mol Biol 2008 June; 15(6): 558-66). The 12mer peptide D-pep (QSHYRHISPAQV) is also representative of larger peptides active in the instant methods. Wiesehan, K., Stohr, J., Nagel-Steger, L., van Groen, T., Riesner, D. and Willbold, D. (2008) Inhibition of cytotoxicity and amyloid fibril formation by a D-amino acid peptide that specifically binds to Alzheimer's disease amyloid peptide. Protein Eng Des Sel 21: 241-6. Additional peptide species, including the double N-methylated analogue of islet amyloid polypeptide (IAPP) IAPP-GI, may find application in the instant methods. Rezaei-Ghaleh N, Andreetto E, Yan L M, Kapurniotu A, Zweckstetter M. Interaction between amyloid beta peptide and an aggregation blocker peptide mimicking islet amyloid polypeptide. PLoS One 2011; 6(5):e20289. Saccharides may also find application in the instant methods, including those simple saccharides mannose, sucrose, and raffinose. Wang M S, Boddapati S, Sierks M R. Antifibrillizing agents catalyze the formation of unstable intermediate aggregates of beta-amyloid. Biotechnol Prog 2010 July; 26(4):1172-9. Polyphenol aglycones, representative of which may include resveratrol, phloretin, naringenin, apigenin, and quercetin may also find use in the instant methods. Ladiwala A R, Mora-Pale M, Lin J C, Bale S S, Fishman Z S, Dordick J S, et al. Polyphenolic Glycosides and Aglycones Utilize Opposing Pathways To Selectively Remodel and Inactivate Toxic Oligomers of Amyloid beta. Chembiochem 2011 Jun. 10. Biflavinoids, such as taiwaniaflavone (TF), 2',8"-biapigenin, amentoflavone, and sumaflavone, are representative of flavones species which may find application in the instant methods. Thapa A, Woo E R, Chi E Y, Sharoar M G, Jin H G, Shin S Y, et al. Biflavonoids are superior to monoflavonoids in inhibiting amyloid-beta toxicity and fibrillogenesis via accumulation of nontoxic oligomer-like structures. Biochemistry 2011 Apr. 5; 50(13): 2445-55.

Moreover, we have determined that the mechanism of action of these compounds is characterized by the formation of innocuous assemblies of the compound itself plus Aβ protein. In atomic force microscopy pictures, these assemblies appear as bulky Aβ protein aggregates. These aggregates are inert and nontoxic to neurons. The assembly of these non-toxic bulky Aβ aggregates happens very rapidly and thereby avoids aggregation of Aβ monomers into pathologic, highly-structured, β-sheet-like oligomers, which finally leads to the therapeutic benefit for patients.

To date, the understanding has been that continuous levels of Aβ aggregation modulators are needed to ensure that toxic Aβ oligomeres can't be formed. However, the present invention is based on the unexpected finding that beneficial treatment effects can also be achieved without continuous levels of Aβ aggregation modulators. In fact, it is sufficient to administer a first effective dose of the Aβ aggregation modulator to initiate the formation of non-toxic bulky Aβ aggregates. Surprisingly, after the first initiation of that pathway, it becomes the major pathway of Aβ processing in the organism and—for a certain amount of time—remains the major pathway even after the aggregation modulators are no longer present. This means that the Aβ aggregation modulators as described above—when applied intervallic—act to initiate a process that is then self-maintaining. After non-toxic bulky Aβ aggregates have once been formed, they act as biological "magnets" to remove soluble Aβ automatically from the organism. In this situation, the processing of Aβ is redirected towards the rapid formation of non-toxic bulky Aβ aggregates even in the absence of pharmacological agents. This continuous detoxification of elevated Aβ levels is the underlying reason for the neuroprotective treatment effect.

Methods comprising the administration of these substances find application in treating patients with various types of ocular disorders including all forms of glaucoma, as aforementioned, and pigmentary dispersion syndrome, pseudoexfoliation syndrome, secondary angle-closure glaucoma, neovascular glaucoma, uveitis, age-related macular degeneration, diabetic retinopthia, degenerative optic neuropathy and other eye pathologies characterized by a progressive loss of vision leading finally to blindness known to those skilled in the art. Such conditions have in common a progressive decline of eye sight related to a degenerative process of retina or optic nerve. Treatment is possible at all stages of disease progression including very early stages as a prophylactic. The clinical effects may be two-fold, first an acute improvement in eye sight in those patients already suffering from a glaucomatous degeneration, and second a slowing-down or stopping of the progressive worsening of the eye-sight. Even patients who experience blindness in one or two eyes related to glaucoma may regain eyesight to some extent.

The instant methods optionally comprise administering preparations containing these substances in certain time intervals. This leads to the formation of fresh non-toxic bulky Aβ aggregates as additional condensation centers for soluble Aβ ("booster" dosing). Depending on the type and the stage of the underlying disease treatment, cycles of some days to several months are possible. Compared to known continuous treatment regimens, the interval therapies of the invention have the following advantages:

A treatment interval with drug dosing every second day up to several times per year only is a distinct improvement in convenience and quality of life for patients compared to dosing required as often as several times per day up to once a day at least. This holds true independent of the route of dosing and type of AB-associated disease.

Patient compliance with interval therapy is also improved. The more often patients have to administer medication, the more they are annoyed by the treatment and simply omit dosing time points. With increased compliance the treatment benefit improves.

The innovative treatment regimen reduces significantly the overall exposure to the drug. Reduced exposure means reduced risk of adverse effects. So, the tolerability and the safety profile can dramatically be increased without loss of beneficial treatment effects.

The total dose of compound to be applied per patient is reduced, which dramatically lowers the production cost.

Alternately, bulky non-toxic Aβ aggregates may be obtained synthetically (synthetic bulky aggregates) or from a conditioned medium of Aβ producing cells. For example, conditioned medium of Aβ producing cells may be incubated with Aβ aggregation modulators.

After the Aβ protein and the respective Aβ aggregation modulator form non-toxic bulky Aβ aggregates, these non-toxic bulky Aβ aggregates may be separated by differential ultracentrifugation/washing (or other suitable techniques such as serial dilution) until all removable Aβ aggregation modulator has been rinsed off. The cleaned and superficially Aβ aggregation modulator-free non-toxic bulky Aβ aggregates may then be administered in place of Aβ aggregation modulators to block the toxic effects of particular neurotoxic Aβ species by promoting further formation of bulky Aβ aggregates.

The instant methods optionally comprise administering at least one additional pharmaceutical agent which is known in the art to be effective in the treatment of ocular disorders. Such administration may be included according to the preferred therapeutic regimen of the at least one additional pharmaceutical agent, independent of the instant interval treatment regimen. These additional agents may be selected from the general class of anti-glaucoma drugs including those mentioned above, antibiotics virostatics, steroids, anti-allergic drugs, artificial tears and other drugs used for local and systemic eye treatment. Representative anti-glaucoma drugs include acetazolamide, diclofenamide, carteolol, timolol, metipranolol, betaxolol, pindolol, levobunolol, brimonidine, clonidine, pilocarpine, carbachol, dipivefrine, apraclonidine, brinzolamide, dorzolaminde, bimatoprost, travaprost, and latanoprost. Representative antibiotics used for eye infections are chlortetracycline, ciprofloxacine, ofloxacine, fusidinic acid, gentamicine, kanamycine, levofloxacine, lomefloxacine, oxytetracycline, natamycine, azidamfenicole, chloramphenicole, tobramycine, erythromycine, and polymyxin-B. Representative virostatics include acaclovir, and trifluridine. Representative steroids include betamethasone, dexamethasone, fluorometholone, hydrocortisone, prednisolone, and rimexolone. Representative anti-allergic drugs include cromoglicate, azelastine, lodoxamide, emedastine, nedocromile, levocabastine, olopatadinea and ketotifene. Representative artificial tears include hypromellose, carbomere, hyaluronate, carmellose, hypromellose, povidone, hyetellose, polivinylalcohole, and dexpanthenole. Other representative commonly used eye therapeutics are tetryzoline, troxerutine, tramazoline, naphazoline, xylometazoline, phenylephrine, antazoline.

The following peptides as described in US Published Application No. US2006/0234947 A1 are representative of those short chain peptides, possibly comprising modified amino acids such as aminoisobutyric acid, described by Gazit, which are discussed above. D-Phe-D-Phe-D-Pro (SEQ ID NO. 1), Aib-D-Phe-D-Asn-Aib (SEQ ID NO. 2), D-Phe-D-Asn-D-Pro (SEQ ID NO. 3), Aib-Asn-Phe-Aib (SEQ ID NO. 4), Gln-Lys-Leu-Val-Phe-Phe (SEQ ID NO. 5), Tyr-Tyr (SEQ ID NO. 6), D-Phe-D-Phe-D-Pro (SEQ ID NO. 7), Aib-D-Phe-D-Asn-Aib (SEQ ID NO. 8), Aib-Asn-Phe-Aib (SEQ ID NO. 9), Tyr-Tyr (SEQ ID NO. 10), Tyr-Tyr-NH$_2$ (SEQ ID NO. 11), Aib-Phe-Phe (SEQ ID NO. 12), Asn-Tyr-Aib (SEQ ID NO. 13), Asn-Tyr-Pro (SEQ ID NO. 14), β-aminoisobutyric acid (Aib)-D-Pro-D-Tyr-D-Asn (SEQ ID NO. 15), D-Tyr-Aib (SEQ ID NO. 16), D-Pro-D-Tyr (SEQ ID NO. 17), D-Tyr-D-Pro (SEQ ID NO. 18), Asn-Tyr-Tyr-Pro (SEQ ID NO. 19), Tyr-Tyr-Aib (SEQ ID NO. 20), Aib-Tyr-Tyr (SEQ ID NO. 21), Aib-Tyr-Tyr-Aib (SEQ ID NO. 22), D-Asn-Tyr-Tyr-D-Pro (SEQ ID NO. 23), Pro-Tyr-Tyr (SEQ ID NO. 24), Tyr-Tyr-Pro (SEQ ID NO. 25), Pro-Tyr-Tyr-Pro (SEQ ID NO. 26), D-Tyr-D-Tyr (SEQ ID NO. 27), D-Pro-Aib (SEQ ID NO. 28), D-Phe-D-Pro (SEQ ID NO. 29), D-Trp-Aib (SEQ ID NO. 30), D-Trp-D-Pro (SEQ ID NO. 31), D-Phe-Pro (SEQ ID NO. 32), and Pro-D-Phe (SEQ ID NO. 33). Unless otherwise noted, the residue Aib is understood to mean α-aminoisobutyric acid.

Additionally, short chain molecules comprising a tryptophan moiety may act as suitable Aβ aggregation modulators. Suitable compounds are described in International Application No. PCT/IL2011/050010 and thus incorporated herein by reference. In particular compounds presented in table 1, the examples and the claims of the application as filed are suitable for use according to the method described herein. For example, the following compounds or their pharmaceutically acceptable salts may be used:

(R)-(tert-butyl 2-(2-amino-3-(1H-indol-3-yl)propanamido)-2-methylpropanoate), (methyl 2-(2-amino-3-(1H-indol-3-yl)-2-methylpropanamido)-2-methylpropanoate), (methyl 1-(2-amino-3-(1H-indol-3-yl)-2-methylpropanamido)cyclopentanecarboxylate), (R)-1-(2-amino-3-(1H-indol-3-yl)propanamido)cyclopentanecarboxylic acid, (R)-(1-(2-amino-3-(1H-indol-3-yl)propanamido)cyclopropanecarboxylic acid), (ethyl 1-(2-amino-3-(1H-indol-3-yl)propanamido)cyclopropanecarboxylate), 1-(2-amino-3-(1H-indol-3-yl)propanamido)cyclohexane carboxylic acid, ethyl 1-(2-amino-3-(1H-indol-3-yl)propanamido)cyclohexane carboxylate, methyl 1-(2-amino-3-(1H-indol-3-yl)propanoyl)-2-methyl-pyrrolidine-2-carboxylate, (R)-3-(2-amino-3-(1H-indol-3-yl)propanamido)oxetane-3-carboxylic acid, (R)-3-(2-amino-3-(1H-indol-3-yl)propanamido)oxetane-3-carboxamide, (R)-2-amino-N-1(1-amino-2-methyl-1-oxopropan-2-yl)-3-(1-H-indol-3-yl)propanamide (R)-3-((2-amino-3-(1H-indol-3-yl)-2,2-dimethyl-hex-3-enoic acid Further suitable compounds are described in International Application No. PCT/EP2011/068820 and thus incorporated herein by reference. In particular compounds presented in the examples and claims of the application as filed are suitable for use according to the method described herein. For example, the following compounds or their pharmaceutically acceptable salts may be used:

N—((R)-2-Amino-3-(1H-indol-3-yl)-propyl)-2,2-dimethyl-malonamic acid, (E)-(R)-5-Amino-6-(1H-indol-3-yl)-2,2-dimethyl-hex-3-enoic-acid, (E)-(R)-5-Amino-6-(1H-indol-3-yl)-2,2-dimethyl-hex-3-enoic acid amide, (E)-(R)-5-Amino-6-(1H-indol-3-yl)-2,2-dimethyl-hex-3-enoic-acid-methylamide, (E)-(R)-5-Acetylamino-6-(1H-indol-3-yl)-2,2-dimethyl-hex-3-enoic-acid, (R)-5-Amino-6-(1H-indol-3-yl)-2,2-dimethyl-4-oxo-hexanoic-acid, (R)-5-Amino-4-hydroxy-6-(1H-indol-3-yl)-2,2-dimethyl-hexanoic-acid, (R,E)-6-(1H-indol-3-yl)-2,2-dimethyl-5-(N-methylacetamide)hex-3-enoic acid, (E)-(R)-5-Acetylamino-6-(1H-indol-3-yl)-2,2-dimethyl-hex-3-enoic-acid-amide, (E)-(R)-5-Acetylamino-6-(1H-indol-3-yl)-2,2-dimethyl-hex-3-enoic-acid-methylamide,
(E)-(S)-5-Amino-6-(1H-indol-3-yl)-2,2-dimethyl-hex-3-enoic-acid-amide,
(E)-(S)-5-Amino-6-(1H-indol-3-yl)-2,2-dimethyl-hex-3-enoic-acid-methylamide
(R)-5-Amino-6-(1H-indol-3-yl)-2,2-dimethyl-4-oxo-hexanoic-acid-methylamide
(R)-5-Acetylamino-6-(1H-indol-3-yl)-2,2-dimethyl-4-oxo-hexanoic acid.

It will be apparent to those skilled in the art that the described substances are merely representative in nature and that alternative substances are known to one of ordinary skill in pharmacology.

The term "analog" or "derivative" is used herein in the conventional pharmaceutical sense, to refer to a molecule that structurally resembles an active substance of the instant method (such as D-Trp-Aib), but has been modified in a targeted and controlled manner to replace one or more specific substituents of the referent molecule with an alternate substituent, thereby generating a molecule which is structurally similar to the referent molecule. Synthesis and screening of analogs (e.g., using structural and/or biochemical analysis), to identify slightly modified versions of a known substance which may have improved or biased traits (such as higher potency and/or selectivity at a specific targeted receptor type, greater ability to penetrate mammalian blood-brain barriers, fewer side effects, etc.) is a drug design approach that is well known in pharmaceutical chemistry.

In addition, using methods known to those skilled in the art, analogs and derivatives of the substances of the invention can be created which have improved therapeutic efficacy in controlling β-amyloid (Aβ) toxicity, i.e., higher potency and/or selectivity at a specific targeted receptor type, either greater or lower ability to penetrate mammalian blood-brain barriers (e.g., either higher or lower blood-brain barrier permeation rate), fewer side effects, etc.

Due to their high degree of activity and their low toxicity, together presenting a most favorable therapeutic index, the substances of the invention may be administered to a subject, e.g., a living animal (including a human) body, in need thereof, for the treatment, alleviation, or amelioration, palliation, or elimination of an indication or condition which is susceptible thereto, or representatively of an indication or condition set forth elsewhere in this application, optionally concurrently, simultaneously, or together with one or more pharmaceutically-acceptable excipients, carriers, or diluents, especially and optionally in the form of a pharmaceutical composition thereof, whether by oral, rectal, or parental (including intravenous, intraocular, and subcutaneous) or in some cases even topical route (including eye drops, eye creams, and intraocular depot formulations), in an effective dose. Suitable dosage ranges include 1-1000 milligrams daily, alternately 10-500 milligrams daily, and optionally 50-500 milligrams daily, depending as usual upon the exact mode of administration, form in which administered, the indication toward which the administration is directed, the subject involved and the body weight of the subject involved, and the preference and experience of the physician or veterinarian in charge.

The term "therapeutically effective" applied to dose or amount refers to that quantity of a substance or pharmaceutical composition that is sufficient to result in a desired activity upon administration to a living animal body (including a human body) in need thereof. The term "treat" is used herein to mean to relieve or alleviate at least one symptom of a disease in a subject. Within the meaning of the present invention, the term "treat" also denotes to arrest, delay the onset (i.e., the period prior to clinical manifestation of a disease) and/or reduce the risk of developing or worsening a disease.

The phrase "pharmaceutically acceptable", as used in connection with compositions of the invention, refers to molecular entities and other ingredients of such compositions which are physiologically tolerable and do not typically produce untoward reactions when administered to a mammal (e.g., human). The term "pharmaceutically acceptable" may also mean approved by a regulatory agency of the Federal or a state government or listed in the U.S. Pharmacopeia or other generally recognized pharmacopeia for use in mammals, and more particularly in humans.

Substances of the present invention may be in the form of pharmaceutically acceptable salts. "Pharmaceutically acceptable salts" refers to those salts which possess the biological effectiveness and properties of the parent compound and which are not biologically or otherwise undesirable. The nature of the salt or isomer is not critical, provided that it is non-toxic and does not substantially interfere with the desired pharmacological activity.

The term "carrier" applied to pharmaceutical compositions of the invention refers to a diluent, excipient, or vehicle with which an active substance (such as D-Trp-Aib) is administered. Such pharmaceutical carriers may be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical carriers are described in "Remington's Pharmaceutical Sciences" by A. R. Gennaro, $20^{th}$ Edition.

The term "about" or "approximately" usually means within 20%, alternatively within 10%, including within 5% of a given value or range. Alternatively, especially in biological systems, the term "about" means within about a log (i.e., an order of magnitude), including within a factor of two of a given value.

In conjunction with the methods of the present invention, also provided are pharmaceutical compositions comprising a therapeutically effective dose of the active substance and/or a sub-therapeutically effective dose of the active substance, e.g., between 0 and 0.75 of the therapeutically effective dose of the active substance. The compositions of the invention may further comprise a carrier or excipient (all pharmaceutically acceptable).

The instant Aβ aggregation modulators or pharmaceutical compositions comprising the same may be used for the treatment of ocular disorders including glaucoma according to the administration scheme of the instant invention. In one embodiment the modulators and/or pharmaceutical composition (medicament) are adapted to or appropriately prepared for a specific administration as disclosed herein (e.g., intervallic treatment, maintenance therapy, once-a-day, twice-a-day administration, or three times a day administration). For this purpose the package and/or the package leaflet and/or the patient information and/or the dosage form itself may contain corresponding information.

The active ingredient (e.g., Aβ aggregation modulators) or the composition of the present invention may be used for the manufacture of a medicament for the treatment of ocular disorders including glaucoma, wherein the medicament is adapted to or appropriately prepared for a specific administration as disclosed herein (e.g., intervallic treatment, maintenance therapy, once-a-day, twice-a-day administration, or three times a day administration). For this purpose the package leaflet and/or the patient information contains corresponding information.

According to the present invention, the dosage form of the active substance may be a solid, semisolid, or liquid formulation according to the following.

The active substance of the instant invention may be administered orally, topically, parenterally, or mucosally (e.g., buccally, by inhalation, or rectally) in dosage unit formulations containing conventional non-toxic pharmaceutically acceptable carriers. In another embodiment for administration to pediatric subjects, the active substance may be formulated as a flavored liquid (e.g., peppermint flavor). The active substance may be administered orally in the form of a capsule, a tablet, or the like, or as a semi-solid, or liquid formulation (see Remington's Pharmaceutical Sciences, 20$^{th}$ Edition, by A. R. Gennaro).

For oral administration in the form of a tablet or capsule, the active substance may be combined with non-toxic, pharmaceutically acceptable excipients such as binding agents (e.g., pregelatinized maize starch, polyvinylpyrrolidone or hydroxypropyl methylcellulose); fillers (e.g., lactose, sucrose, glucose, mannitol, sorbitol and other reducing and non-reducing sugars, microcrystalline cellulose, calcium sulfate, or calcium hydrogen phosphate); lubricants (e.g., magnesium stearate, talc, or silica, steric acid, sodium stearyl fumarate, glyceryl behenate, calcium stearate, and the like); disintegrants (e.g., potato starch or sodium starch glycolate); or wetting agents (e.g., sodium lauryl sulphate), coloring and flavoring agents, gelatin, sweeteners, natural and synthetic gums (such as acacia, tragacanth or alginates), buffer salts, carboxymethylcellulose, polyethyleneglycol, waxes, and the like.

The tablets may be coated with a concentrated sugar solution which may contain e.g., gum arabic, gelatine, talcum, titanium dioxide, and the like. Alternatively, the tablets may be coated with a polymer that dissolves in a readily volatile organic solvent or mixture of organic solvents. In specific embodiments, the active substance is formulated into immediate-release (IR) or modified-release (MR) tablets. Immediate release solid dosage forms permit the release of most or all of the active ingredient over a short period of time, such as 60 minutes or less, and make rapid absorption of the drug possible. Modified release solid oral dosage forms permit the sustained release of the active substance over an extended period of time in an effort to maintain therapeutically effective plasma levels over similarly extended time intervals and/or to modify other pharmacokinetic properties of the active substance.

For the formulation of soft gelatin capsules, the active substances may be admixed with e.g., a vegetable oil or poly-ethylene glycol. Hard gelatin capsules may contain granules of the active substances using either the above mentioned excipients for tablets e.g., lactose, saccharose, sorbitol, mannitol, starches (e.g., potato starch, corn starch or amylopectin), cellulose derivatives or gelatine. Also liquids or semisolids of the drug may be filled into hard gelatine capsules.

The compositions of the invention may also be introduced in microspheres or microcapsules, e.g., fabricated from polyglycolic acid/lactic acid (PGLA) (see, e.g., U.S. Pat. Nos. 5,814,344; 5,100,669 and 4,849,222; PCT Publications No. WO 95/11010 and WO 93/07861). Biocompatible polymers may be used in achieving controlled release of an active substance, include for example, polylactic acid, polyglycolic acid, copolymers of polylactic and polyglycolic acid, polyepsilon caprolactone, polyhydroxybutyric acid, polyorthoesters, polyacetals, polyhydropyrans, polycyanoacrylates, and cross-linked or amphipathic block copolymers of hydrogels.

Formulation of an active substance in a semi-solid or liquid form may also be used. The substance may constitute between 0.1 and 99% by weight of the formulation, more specifically between 0.5 and 20% by weight for formulations intended for injection and between 0.2 and 50% by weight for formulations suitable for oral administration.

In one embodiment of the invention, the active substance is administered in a modified release formulation. Modified release dosage forms provide a means for improving patient compliance and for ensuring effective and safe therapy by reducing the incidence of adverse drug reactions. Compared to immediate release dosage forms, modified release dosage forms can be used to prolong pharmacologic action after administration, and to reduce variability in the plasma concentration of a drug throughout the dosage interval, thereby eliminating or reducing sharp peaks.

A modified release dosage form may comprise a core either coated with or containing an active substance. The core being is then coated with a release modifying polymer within which the active substance is dispersed. The release modifying polymer disintegrates gradually, releasing the active substance over time. Thus, the outer-most layer of the composition effectively slows down and thereby regulates the diffusion of the active substance across the coating layer when the composition is exposed to an aqueous environment, i.e. the gastrointestinal tract. The net rate of diffusion of the active substance is mainly dependent on the ability of the gastric fluid to penetrate the coating layer or matrix and on the solubility of the active substance itself.

In another embodiment of the invention, the active substance is formulated in an oral, liquid formulation. Liquid preparations for oral administration can take the form of, for example, solutions, syrups, emulsions or suspensions, or they can be presented as a dry product for reconstitution with water or other suitable vehicle before use. Preparations for oral administration can be suitably formulated to give controlled or postponed release of the active compound.

For oral administration in liquid form, the active substance may be combined with non-toxic, pharmaceutically acceptable inert carriers (e.g., ethanol, glycerol, water), suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), preservatives (e.g., methyl or propyl-p-hydroxybenzoates or sorbic acid), and the like. Stabilizing agents such as antioxidants (BHA, BHT, propyl gallate, sodium ascorbate, citric acid) may also be added to stabilize the dosage forms. For example, solutions may contain from about 0.2% to about 20% by weight of the active substance, with the balance being sugar and mixture of ethanol, water, glycerol and propylene glycol. Optionally, such liquid formulations may contain coloring agents, flavoring agents, saccharine and carboxymethyl-cellulose as a thickening agent or other excipients.

In another embodiment, a therapeutically effective dose of the active substance is administered in an oral solution containing a preservative, a sweetener, a solubilizer, and a solvent. The oral solution may include one or more buffers, flavorings, or additional excipients. In a further embodiment, a peppermint or other flavoring is added to the active substance oral liquid formulation.

For administration by inhalation, the active substance may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered dose. Capsules and cartridges of, e.g., gelatin for use in an inhaler or insufflator can be formulated containing a powder mix of the compound and a suitable powder base such as lactose or starch.

Solutions for parenteral applications by injection may be prepared in an aqueous solution of a water-soluble pharmaceutically acceptable salt of the active substances, preferably in a concentration of from about 0.5% to about 10% by weight. These solutions may also contain stabilizing agents and/or buffering agents and may conveniently be provided in various dosage unit ampoules.

The formulations of the invention may be delivered parenterally, i.e., by intraocular, intravenous (i.v.), intracerebroventricular (i.c.v.), subcutaneous (s.c.), intraperitoneal (i.p.), intramuscular (i.m.), subdermal (s.d.), or intradermal (i.d.) administration, by direct injection, via, for example, bolus injection or continuous infusion. Formulations for injection can be presented in unit dosage form, e.g., in ampoules or in multi-dose containers, with an added preservative. Alternatively, the active ingredient may be in powder form for reconstitution with a suitable vehicle, e.g., sterile pyrogen-free water, before use.

The invention also provides a pharmaceutical pack or kit comprising one or more containers containing the active substance and, optionally, more of the ingredients of the formulation. In a specific embodiment, the active substance is provided as an oral solution (for example 2 mg/ml) for administration with the use of a 2 teaspoon capacity syringe (dosage KORC®). Each oral syringe has hatch marks for measurement, with lines on the right side of the syringe (tip down) representing tsp units, and those on the left representing ml units.

The optimal therapeutically effective dose may be determined experimentally, taking into consideration the exact mode of administration, from in which the drug is administered, the indication toward which the administration is directed, the subject involved (e.g., body weight, health, age, sex, etc.), and the preference and experience of the physician or veterinarian in charge.

Dosage units for rectal application may be solutions or suspensions or may be prepared in the form of suppositories or retention enemas comprising the substances of the invention in a mixture with a neutral fatty base, or gelatin rectal capsules comprising the active substances in admixture with vegetable oil or paraffin oil.

Toxicity and therapeutic efficacy of the compositions of the invention may be determined by standard pharmaceutical procedures in experimental animals, e.g., by determining the LD50 (the dose lethal to 50% of the population) and the ED50 (the dose therapeutically effective in 50% of the population). The dose ratio between therapeutic and toxic effects is the therapeutic index and it may be expressed as the ratio LD50/ED50. Compositions that exhibit large therapeutic indices are preferred.

Suitable effective doses of the active substance of the invention in therapeutic treatment of humans are about 0.01-10 mg/kg bodyweight on peroral administration and 0.001-10 mg/kg bodyweight on parenteral administration.

Treatment duration may be short-term, e.g., several weeks (for example 8-14 weeks), or long-term until the attending physician deems further administration no longer is necessary.

The active substance of the instant invention may be administered as a monotherapy, or in combination with another substance prescribed for the treatment of an optical condition associated with β-amyloid (Aβ) toxicity or, more specifically, glaucoma.

The term "combination" applied to active substances is used herein to define a single pharmaceutical composition (formulation) comprising two active substances (e.g., a pharmaceutical composition comprising an active substance as described herein and another substance prescribed for the treatment of an optical condition associated with β-amyloid (Aβ) toxicity or, more specifically, glaucoma) or two separate pharmaceutical compositions, each comprising an active substance (e.g. a pharmaceutical composition comprising a an active substance of the instant invention or another substance prescribed for the treatment of an optical condition associated with β-amyloid (Aβ) toxicity or, more specifically, glaucoma), to be administered conjointly.

Within the meaning of the present invention, the term "conjoint administration" is used to refer to administration of an active substance as described herein and a second active substance (e.g. another substance prescribed for the treatment of an optical condition associated with β-amyloid (Aβ) toxicity or, more specifically, glaucoma) simultaneously in one composition, or simultaneously in different compositions, or sequentially. For the sequential administration to be considered "conjoint", however, an active substance as described herein and the second active substance must be administered separated by a time interval which still permits the resultant beneficial effect for treating an optical condition associated with β-amyloid (Aβ) toxicity in a mammal. The invention encompasses such combination administration strategy wherein the Aβ aggregation modulators are administered at therapeutically effective doses, therapeutically sub-effective doses or not administered at all during specific days of such "combination" therapy.

The Experimental substances of the instant invention may be useful for the treatment of glaucoma and also age-related RGC dysfunction as the role of Aβ has also been suggested for the latter condition. Moreover, plausible synergistic therapeutic effects can be expected from a combined treatment with intraocular pressure lowering agents currently used in glaucoma as well as proposed future therapies such as antioxidants, calcium channel blockers, NO synthase inhibitors, neurotrophins and antiapoptotic.

The present invention provides novel, valuable, and surprising applications and uses for substances in the methods of the present invention, as well as novel pharmaceutical compositions thereof, possessed of at least one of the herein-described characteristics and/or advantages.

The method-of-treating a living animal body with a substance of the invention, for the inhibition of progression or alleviation of the selected ailment therein, is as previously stated by any normally-accepted pharmaceutical route, employing the at least one selected dosage which is effective in the alleviation of the particular ailment desired to be alleviated followed by some period of sub-effective dosage or no dosage.

Use of the substances of the present invention in the manufacture of a medicament for the treatment of a living animal for inhibition of progression or alleviation of selected ailments or conditions, particularly ailments or conditions such as optical conditions associated with β-amyloid (Aβ) toxicity, is carried out in the usual manner comprising the step of admixing an effective dose of a compound of the invention with a pharmaceutically-acceptable diluent, excipient, or carrier, and the method-of-treating, pharmaceutical compositions, and use of a compound of the present invention in the manufacture of a medicament.

Representative pharmaceutical compositions prepared by admixing the active substance with a suitable pharmaceutically-acceptable excipient, diluent, or carrier, include tablets, capsules, solutions for injection, liquid oral formulations, aerosol formulations, TDS formulations, and nanoparticle formulations, thus to produce medicaments for oral, injectable, or topical use, also in accord with the foregoing.

PHARMACOLOGY—SUMMARY

The method of using the active substances of the present invention, and pharmaceutical compositions thereof, are characterized by unique advantageous and unpredictable properties, rendering the "subject matter as a whole", as claimed herein, unobvious. The methods and pharmaceutical compositions therefore have exhibited, in standard accepted reliable test procedures, the following valuable properties and characteristics:

Pharmacological Example 1

Methods

In experimental model of glaucoma, there is increased expression of amyloid precursor protein (APP) and likely related apoptosis in retinal ganglion cells (RGC) [McKinnon, S. J.; Lehman, D. M.; Kerrigan-Baumrind, L. A.; Merges, C. A.; Pease, M. E.; Kerrigan, D. F.; Ransom, N. L.; Tahzib, N. G.; Reitsamer, H. A.; Levkovitch-Verbin, H.; Quigley, H. A., and Zack, D. J. Caspase activation and amyloid precursor protein cleavage in rat ocular hypertension. Invest Ophthalmol Vis Sci. 2002 April; 43(4):1077-87]. Furthermore, injection of $A\beta_{1-42}$ induces apoptosis in RGC. Interference with APP-Aβ pathway such as ocular application of antibody, inhibition of β-secretase activity or oligomerisation inhibition prevents, at least temporally RGC apoptosis in glaucoma resulting from increased ocular pressure (Guo, et al., 2007).

Experimental Procedure

In the male Dark Aguti rat model, glaucoma is produced by injection of hypertonic saline into episcleral veins of one eye to induce increased ocular pressure (chronic ocular hypertension—OHT), while the opposite eye serves as a control [Morrison J. C., Moore C. G., Deppmeier L. M., Gold B. G., Meshul C. K., Johnson E. C. A rat model of chronic pressure-induced optic nerve damage. Exp Eye Res. 1997; 64(1): 85-96] In treatment groups (N=4-8 per group), various doses of substances of the instant invention are injected intravitreally (in 5 μl volume) at the time of glaucoma induction and in some groups the administration continues for following 7 days to see whether such extended treatment results in increased efficacy. The extent of RGC apoptosis at 3 weeks and 6 weeks after chronic ocular hypertension (OHT) induction is assessed in each animal by dynamic confocal scanning laser ophthalmoscopy and fluorescent-labeled Annexin V. Animals are sacrificed after 3 and 6 weeks and their eyes are enucleated and fixed in 4% paraformaldehyde overnight. Afterwards, retinas are separated for assessing apoptosis related changes, for example: as visualised with FITC Annexin V kit (BD Biosciences, Franklin Lakes, USA) [Cordeiro, M. F., Guo, L., Luong, V., Harding, G., Wang, W., Jones, H. E., Moss, S. E., Sillito, A. M., and Fitzke, F. W. 2004 Real-time imaging of single nerve cell apoptosis in retinal neurodegeneration. Proc Natl Acad Sci USA, 101, 13352-6; Kietselaer, B. L., Hofstra, L., Dumont, E. A., Reutelingsperger, C. P., and Heidendal, G. A. 2003 The role of labeled Annexin A5 in imaging of programmed cell death. From animal to clinical imaging. Q J Nucl Med, 47, 349-61], or TUNEL (dUTP nick end labeling) [Roche, In situ cell death detection kit, fluorescein labelled] [Szydlowska K., Kaminska B., Baude A., Parsons C. G., Danysz W. 2007 Neuroprotective activity of selective mGlu1 and mGlu5 antagonists in vitro and in vivo. Eur. J. Pharmacol. 554, 18-29.]. In animals treated with experimental substances of the instant invention, there is a decrease in RGC apoptosis at least at one time point assessed.

In a further experiment, rats are treated systemically (s.c.) and the experiment is repeated as above. The aim of this study is to verify whether systemic administration produces sufficiently high concentrations in the eye. Therefore, additionally, concentrations of substances of the instant invention are analyzed in the vitreal space of the eye. In animals treated systemically with experimental substances, there is a decrease in RGC apoptosis at least at one time point assessed and significant concentrations of the experimental substances are detected in the vitreal space of the eye.

The experiment is repeated as described above, except that substance is applied (s.c.) once 24 hrs before induction of glaucoma. Studies show that at the point in time when glaucoma is induced, the concentration of the applied substance in the eye is negligible. Surprisingly, such treatment is followed by a decrease in RGC loss vs. control when assessed at a certain point in time, e.g. after 3 weeks.

In Vitro Experiment 1

Additionally, effects of experimental substances on toxicity of RGC cells is verified in vitro. Aβ is preaggregated for 1-7 days with an experimental substance (300, 100, 30, 10, 3, 1, 0.3 μM) or vehicle and then part of this solution is added to primary RGC culture for 48 hours to produce a final concentration of A13=1 μM. During this incubation, cells stay in an incubator at 37° C., 95% humidity and 5% CO2. Afterwards, apoptosis/necrosis is verified using FITC Annexin V kit (BD Biosciences, Franklin Lakes, USA) and optionally with propidium iodide [Szydlowska et al., 2007].

In Vitro Experiment 2

Alternatively, effects of experimental substances on toxicity to retinal ganglion cells (RGC) may be verified in vitro using RGC membrane potential recorded by the perforated patch clamp technique as described below. This technique gives the opportunity to monitor the cell membrane potential for a long time since the cytoplasm dialysis is reduced by the perforations in the membrane formed by the antibiotic. Thereby the membrane is permeable only to small cations.

Aβ is prepared from lyophilized Aβ1-42 from Bachem (cod. H-1368 lot number 1030255) which is dissolved in HFIP (Sigma Aldrich) at a concentration of 1 mg/ml. In the experiments Aβ concentration is normally set to 50 nM. Aβ is used after 90 minutes incubation at 36° C. and in any case within 2 hours from the moment in which it was diluted in the physiological bath solution.

RGCs are isolated from neonatal (P5-P6) mouse retinae. The standardized procedure offered by the Miltenyi Biotec kit is used to isolate RGCs. At the end of four days in culture RGCs are identified by the presence of one long protrusion that represents the axon.

Before patch clamp recording, the culture medium bathing the cells is substituted with an external recording solution (140 mM NaCl, 2.5 KCl, 1.8 CaCl2, 0.5 MgCl2, 10 Glucose, 10 Hepes, pH 7.4). The patch clamp experiments are performed using the antibiotic gramicidin (Sigma Aldrich) diluted in an intracellular solution (140 mM KCl, 10 NaCl, 2 MgCl2, 0.1 CaCl2, 10 Glucose, 10 Hepes, pH 6.9) at a final concentration of 5 μg/ml. This solution is used to fill the patch pipette to open pores in the membrane during a "perforated patch-clamp procedure". At said gramicidin concentration, electrical access to the cell is obtained after about 5-10 minutes.

First the resting potential of RGCs in control conditions is measured. The custom made U-tube perfusion apparatus is directed towards the cell under observation and complete changes to the solution perfusing the retinal ganglion cell are achieved in less than 1 second.

The following compounds (e.g. (E)-(R)-5-Amino-6-(1H-indol-3-yl)-2,2-dimethyl-hex-3-enoic-acid, (R)-2-amino-N-1(1-amino-2-methyl-1-oxopropan-2-yl)-3-(1-H-indol-3-yl) propanamide and (R)-3-((2-amino-3-(1H-indol-3-yl)-2,2-dimethyl-hex-3-enoic acid, D-Trp-Aib (SEQ ID NO. 30)) action on beta amyloid stimulated retinal ganglion cells is evaluated as described above. An example for the protective effects of D-Trp-Aib is illustrated in FIG. 1. Aβ1-42 50 nM (pre-incubated for 90 minutes at 36° C.) depolarized isolated retinal ganglion cells (RGC)—arrows shows time point of Aβ1-42 application—FIG. 1A. After a variable time, between 2 and 10 minutes, the cell resting potential moves towards more positive potentials. In FIG. 1B it is clear that the AB1-42 depolarizing effect of Aβ1-42 is prevented by 1 μM D-Trp-Aib co-incubation (90 minutes at 36° C.). FIG. 1C illustrates average resting potential of RGCs under control conditions, in 50 nM Aβ and at two different concentrations of D-Trp-Aib. The difference between control conditions (−59.4±2.8 mV) and Aβ stimulation (35.6±1.8 mV) is highly significant (n=5, p=0.01). No significant difference is found between Aβ application and Aβ plus 0.5 μM D-Trp-Aib (−39.3±1.8 mV). However, the average resting membrane potential of RGCs stimulated with Aβ 50 nM plus 1 μM D-Trp-Aib (−48.9±2.4 mV) is statistically different from the control (n=5, p=0.05), from Aβ stimulation alone (n=5, p=0.05) and from Aβ plus 0.5 μM D-Trp-Aib (n=5, p=0.05). These results demonstrate that D-Trp-Aib protects against Aβ1-42 toxicity.

These data strongly suggest that experimental substances of the instant invention may be useful for the treatment of glaucoma and also age-related RGC dysfunction as the role of Aβ has been suggested for the latter condition as well [Guo, et al., 2007]. Moreover, plausible synergistic therapeutic effects can be expected from a combined treatment with intraocular pressure lowering agents currently used in glaucoma as well as proposed future therapies such as antioxidants, calcium channel blockers, NO synthase inhibitors, neurotrophins and antiapoptotic agents [Hartwick A. T. 2001. Beyond intraocular pressure: neuroprotective strategies for future glaucoma therapy. Optom Vis Sci 78, 85-94.].

Pharmacological Example 2

Experimental Procedure
Method of Producing Synthetic Bulky Aggregates

Aβ1-42 (order number 62-0-80, batch Y11042T1, American Peptide Company, Sunnyvale, Calif. 94086, U.S.A.) is suspended in 100% HFIP (Sigma Aldrich) to approximately 1 mg/ml (2 mg dissolved in 2 ml HFIP) and shaken at 37° C. for 1.5 hours in tightly sealed Eppendorf vials. This is allowed to cool to room temperature and then the solution is portioned into aliquots and the HFIP removed by evaporation using a Speedvac for approximately 30 minutes. When dry, the Aβ1-42 is stored at −20° C. The Aβ1-42 is dissolved in anhydrous DMSO (Sigma Aldrich) to a concentration of 100 fold that required in PBS (i.e. 10 mM for 100 μM) with the aid of an ultrasonic water bath with/without D-Trp-Aib (SEQ ID NO. 30) (i.e. for a 10:1 ratio with D-Trp-Aib (SEQ ID NO. 30) 100 mM for 10 mM Aβ1-42). This solution is then immediately diluted in PBS to a final concentration of 100 μM Aβ in 1% DMSO. These solutions are allowed to aggregate at room temperature for various times (e.g. 1 hour, 1 day, 1 week) before being used.

After aggregation in PBS, solutions are serially diluted in PBS 10 fold and then "recharged" with Aβ1-42 to remove D-Trp-Aib (SEQ ID NO. 30) but maintain the total Aβ1-42 concentration. This Aβ1-42 seed transfer step is repeated at least 4 times, so that final residual concentration of D-Trp-Aib (SEQ ID NO. 30) are 10,000 lower than the starting concentration (e.g. 1 μM reduced to 0.1 nM).

The resulting solution contains mainly toxic oligomeric species/seeds in the case of Aβ1-42 alone but also non-toxic/detoxifying Aβ1-42 seeds in the case of solutions treated with D-Trp-Aib (SEQ ID NO. 30). The cleaned and superficially D-Trp-Aib (SEQ ID NO. 30)—free non-toxic bulky Aβ aggregates are used as the active agent for in vitro or animal experiments either as they are or following further dilution.

The procedure is equally applicable to obtain bulky aggregates by using any of the other Aβ aggregation modulators disclosed herein, for example using (E)-(R)-5-Amino-6-(1H-indol-3-yl)-2,2-dimethyl-hex-3-enoic-acid, (R)-2-amino-N-1 (1-amino-2-methyl-1-oxopropan-2-yl)-3-(1-H-indol-3-yl)propanamide and (R)-3-((2-amino-3-(1H-indol-3-yl)-2,2-dimethyl-hex-3-enoic acid.

Method of Producing Bulky Aggregates from Conditioned Medium Producing Cells

Conditioned medium of Aβ producing cells is incubated with appropriate concentrations of various Aβ aggregation modulators, i.e. D-Trp-Aib (SEQ ID NO. 30), (E)-(R)-5-Amino-6-(1H-indol-3-yl)-2,2-dimethyl-hex-3-enoic-acid, (R)-2-amino-N-1(1-amino-2-methyl-1-oxopropan-2-yl)-3-(1-H-indol-3-yl)propanamide and (R)-3-((2-amino-3-(1H-indol-3-yl)-2,2-dimethyl-hex-3-enoic acid, and others. After several hours of incubation Aβ protein and the respective Aβ aggregation modulator form non-toxic bulky Aβ aggregates as described above. These non-toxic bulky Aβ aggregates are separated by differential ultracentrifugation/washing (or other suitable techniques such as serial dilution) until all removable D-Trp-Aib (SEQ ID NO. 30) (or other Aβ aggregation modulator) is rinsed off. The cleaned and superficially D-Trp-Aib (SEQ ID NO. 30)-free non-toxic bulky Aβ aggregates are used as active agent for in vitro or animal experiments, either as they are or following further dilution.

Method of Confirming Protective Effects of D-Trp-Aib (SEQ ID NO. 30)—Free Non-Toxic Bulky Aβ Aggregates Transverse hippocampal slices (350 μM thick) are obtained from adult (2 month) mice that are ether-anesthetized and decapitated. The brain is rapidly removed, and slices are prepared in ice-cold Ringer solution using a vibroslicer. All slices are placed in a holding chamber for at least 60 min and then transferred to a superfusing chamber for extracellular or whole-cell recordings. The flow rate of the solution through the chamber is 1.5 ml/min. The composition of the solution is 124 mM NaCl, 3 mM KCl, 26 mM NaHCO3, 2 mM CaCl2, 1 mM MgSO4, 10 mM D-glucose, and 1.25 mM NaH2PO4, bubbled with a 95% O2-5% CO2 mixture, and has a final pH of 7.3. All experiments are performed at room temperature.

Extracellular recordings of field excitatory postsynaptic potentials (fEPSPs) are obtained from the dendritic region of the CA1 region of the hippocampus using glass micropipettes (1-2 MW) filled with superfusion solution. Recordings are amplified, filtered (3 kHz), and digitized (9 kHz).

Amplified fEPSPs and NMDA-EPSCs are filtered (3 kHz), digitized (15 kHz) and measured and plotted online, using the "LTP-program"-software. Measurements of the slope of the fEPSP are taken between 20 and 80% of the peak amplitude. Slopes of fEPSPs are normalized with respect to the 30-min control period before tetanic stimulation For long-term potentiation (LTP) induction, high-frequency stimulation conditioning pulses (100 Hz; 4-5 V) are applied to the Schaffer collateral-commissural pathway. Steady baseline recordings are made for at least 30 minutes before application of tetanic stimuli. Aβ1-42 is prepared as described in "Method of producing synthetic bulky aggregates" with or without D-Trp-Aib (SEQ ID NO. 30) and added to the bath solution (giving a final Aβ1-42 concentration of 50-100 nM), 90 min before induction of LTP.

Figure 2:
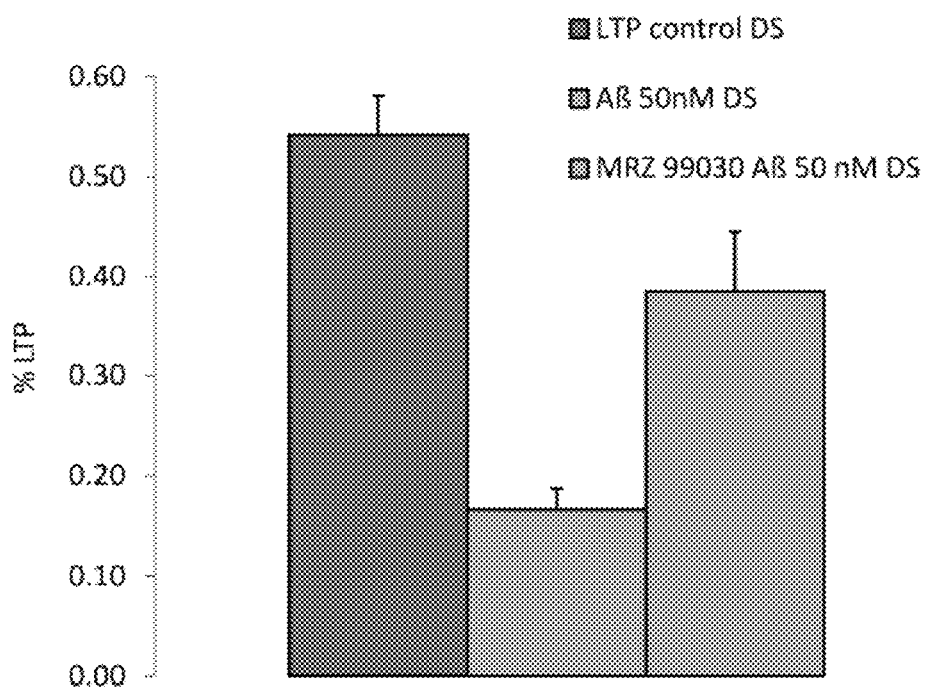
FIG. 2 shows the effect of D-Trp-Aib on long-term potentiation (LTP) inhibition.

As illustrated in FIG. 2. Tetanic stimulation results in strong LTP under control conditions. Prior incubation with Aβ1-42 50 nM aggregated under serial dilution conditions without D-Trp-Aib causes a strong inhibition of LTP. Aβ1-42 50 nM aggregated following "seeding" with D-Trp-Aib serial dilution conditions (starting concentration of D-Trp-Aib=1 µM, final concentration of D-Trp-Aib=0.1 nM) produces significantly less inhibition of LTP (unpaired two-tailed Student t-Test, p=0.0184).

These results demonstrate the toxic effect of Aβ1-42 on fEPSP's and the corresponding protection resulting from administration of the synthetic bulky aggregates.
Treatment with Bulky Aggregates In the male Dark Aguti rat glaucoma model as described above, the non-toxic bulky aggregates as described above, such as D-Trp-Aib (SEQ ID NO. 30)-free non-toxic bulky Aβ aggregates, may be applied by via intravitreal injection in order to provide long lasting beneficial effects on the decrease of RGC apoptosis.

Pharmacological Example 3

Utilizing the rat model of glaucoma noted in Pharmacological Example 1 (Morrison model) glaucoma is induced by application of hypertonic saline into the episcleral vein of the eye. This leads to a long-lasting increase of intraocular pressure and as a consequence to Aβ-associated neurodegeneration of retinal ganglion cells. The cleaned and superficially D-Trp-Aib (SEQ ID NO. 30)-free non-toxic bulky Aβ aggregates (produced as described above) are injected intraocularly into the rat's eyes and thereby reduce significantly the Aβ-induced apoptosis of retinal ganglion cells.

Further animal experiments demonstrate that intermittent application of D-Trp-Aib (SEQ ID NO. 30) or other Aβ aggregation modulators in time intervals of 3 days up to 4 weeks (and even longer) protects against Aβ toxicity with the same efficacy as burdensome continuous treatment with several applications per day.

Pharmacological Example 4

In another animal study with glaucomatous rats (procedure as described above, Morrison model) D-Trp-Aib (SEQ ID NO. 30) is applied 3 days prior to the induction of glaucoma (one single s.c injection). Although D-Trp-Aib (SEQ ID NO. 30) (halflife of 1-2 hours in the rat) is no longer detectable in the animal at the time point of glaucoma induction, it provides a strong neuroprotective effect for retinal ganglion cells. The explanation of this unexpected finding is that the pretreatment with D-Trp-Aib (SEQ ID NO. 30) leads to formation of non-toxic bulky Aβ aggregates (possibly micro non-toxic bulky Aβ aggregates) consisting of D-Trp-Aib (SEQ ID NO. 30) and physiologically Aβ that is ubiquitously prevailing at low concentrations. These non-toxic bulky Aβ aggregates function in isolating toxic Aβ after glaucoma induction even if the Aβ is released at higher concentrations.

The Aβ modulator function is consistent over different application routes including oral, subcutaneous, intraperitoneal, intraveneous, intramuscular (including depot), subconjunctival, topical (e.g. eye drops, gels, implants, modified contact lenses etc.) and other pharmaceutical formulations.

Based on the positive outcome of the above-described prototypical models for Aβ-associated neurodegenerative diseases it may be concluded that the innovative neuroprotective mechanism is effective in other Aβ-associated diseases as well, particularly in macular degeneration of the eye (AMD).

CONCLUSIONS

In conclusion, from the foregoing, it is apparent that the present invention provides novel, valuable, and surprising applications and uses for substances in the methods of the present invention, as well as novel pharmaceutical compositions thereof, all possessed of the foregoing more specifically-enumerated characteristics and advantages.

The high order of activity of the described methods for using the active substances of the present invention and compositions thereof, as evidenced by the tests reported, is indicative of utility. Clinical evaluation in human beings has not been completed, however. It will be clearly understood that the distribution and marketing of any substance or composition falling within the scope of the present invention for use in human beings will of course have to be predicated upon prior approval by governmental agencies, such as the U.S. Federal Food and Drug Administration, which are responsible for and authorized to pass judgment on such questions.

The method-of-treating a living animal body as described herein, for the inhibition of progression or alleviation of the selected ailment therein, is as previously stated by any normally-accepted pharmaceutical route, employing the selected dosage and administration regime which is effective in the alleviation of the particular ailment desired to be alleviated.

Use of the bulky aggregates of the present invention in the manufacture of a medicament for the treatment of a living animal for inhibition of progression or alleviation of selected ailments or conditions, particularly ailments or conditions such as optical conditions associated with β-amyloid (Aβ) toxicity, is carried out in the inventive intervallic manner comprising the step of optionally admixing an effective dose of a compound of the invention with a pharmaceutically-acceptable diluent, excipient, or carrier, and the method-of-treating, pharmaceutical compositions, and use of a compound of the present invention in the manufacture of a medicament.

Representative pharmaceutical compositions prepared by optionally admixing the active substance with a suitable pharmaceutically-acceptable excipient, diluent, or carrier, include tablets, capsules, solutions for injection, liquid oral formulations, aerosol formulations, TDS formulations, and nanoparticle formulations, thus to produce medicaments for oral, injectable, or topical use, also in accord with the foregoing.

The present invention is not to be limited in scope by the specific embodiments described herein. Indeed, various modifications of the invention in addition to those described herein will become apparent to those skilled in the art from the foregoing description.

All patents, applications, publications, test methods, literature, and other materials cited herein are hereby incorporated by reference.

The invention claimed is:

1. A method for the treatment of at least one optical condition associated with β-amyloid (Aβ) toxicity in a subject in need thereof, the method comprising administering to the subject the peptide D-Trp-Aib (SEQ ID NO. 30), which peptide is administered daily for a first period of at least one (1) day in at least a therapeutically effective dose, followed by a second period of at least one (1) week wherein the peptide is not administered,
   followed by repeating said first period of at least one (1) day wherein said peptide is administered daily, wherein said peptide is not administered as a depot,
   and wherein said at least one optical condition is selected from the group consisting of primary angle-closure glaucoma, secondary open-angle glaucoma, wide-angle glaucoma, steroid-induced glaucoma, traumatic glaucoma, pigmentary dispersion syndrome, pseudo-exfoliation syndrome, secondary angle-closure glaucoma, neovascular glaucoma, uveitis and glaucoma, age-related macular degeneration, and diabetic retinopathy.

2. The method of claim 1, wherein the administration of the therapeutically effective dose of the peptide during the first period is continued for at least one week.

3. The method of claim 1, wherein the administration of the therapeutically effective dose of the peptide during the first period is continued for at most one month.

4. The method of claim 1, wherein the second period is at least one (1) month, or at least 2 months.

5. The method of claim 1, wherein the second period is at most 3 months, or at most 6 months, or at most 1 year.

6. The method of claim 1, wherein the second period is from three (3) to six (6) months.

7. The method of claim 1, wherein the peptide is in the form of a pharmaceutically acceptable salt.

8. The method of claim 1, wherein the peptide or pharmaceutically acceptable salt thereof is administered in the form of several single doses administered within a period of time consisting of one (1) or more days.

9. The method of claim 1, wherein the peptide or pharmaceutically acceptable salt thereof is administered at different dose strengths selected from up and down titration.

10. The method of claim 1, wherein the peptide or pharmaceutically acceptable salt thereof is administered in an immediate release formulation.

11. The method of claim 1, wherein the at least one optical condition treated is selected from the group consisting of primary angle-closure glaucoma, and wide-angle glaucoma.

12. The method of claim 1, wherein the peptide is administered in combination in both the first and/or second periods with a therapeutically effective dose of at least one additional pharmaceutical agent which is effective in treating at least one optical condition.

13. The method of claim 12, wherein the at least one additional pharmaceutical agent is a medication administered to treat eye diseases and contains at least one agent selected from anti-glaucoma drugs, antibiotics, anti-inflammatory drugs, steroids, anti-allergic drugs and artificial tear fluid.

14. The method of claim 12, wherein the at least one additional pharmaceutical agent is selected from acetazolamide, diclofenamide, carteolol, timolol, metipranolol, betaxolol, pindolol, levobunolol, brimonidine, clonidine, pilocarpine, carbachol, dipivefrine, apraclonidine, brinzolamide, dorzolaminde, bimatoprost, travaprost, latanoprost, chlortetracycline, ciprofloxacine, ofloxacine, fusidinic acid, gentamicine, kanamycine, levofloxacine, lomefloxacine, oxytetracycline, natamycine, azidamfenicole, chloramphenicole, tobramycine, erythromycine, polymyxin-B, acaclovir, trifluridine, betamethasone, dexamethasone, fluorometholone, hydrocortisone, prednisolone, rimexolone, cromoglicate, azelastine, lodoxamide, emedastine, nedocromile, levocabastine, olopatadinea, ketotifene, hypromellose, carbomere, hyaluronate, carmellose, hypromellose, povidone, hyetellose, polyvinylalcohol, dexpanthenole, tetryzoline, troxerutine, tramazoline, naphazoline, xylometazoline, phenylephrine and antazoline.

15. The method of claim 1, wherein said peptide is administered by injection.

\* \* \* \* \*

```
                              SEQUENCE LISTING

<160> NUMBER OF SEQ ID NOS: 33

<210> SEQ ID NO 1
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(3)
<223> OTHER INFORMATION: Stereoisomer D

<400> SEQUENCE: 1

Phe Phe Pro
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (2)..(3)
<223> OTHER INFORMATION: Stereoisomer D
<220> FEATURE:
<221> NAME/KEY: misc_feature
<222> LOCATION: (4)..(4)
<223> OTHER INFORMATION: Alpha-aminoisobutyric acid (Aib)

<400> SEQUENCE: 2

Xaa Phe Asn Xaa
1

<210> SEQ ID NO 3
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(3)
<223> OTHER INFORMATION: Stereoisomer D

<400> SEQUENCE: 3

Phe Asn Pro
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Alpha-aminoisobutyric acid (Aib)
```

```
<220> FEATURE:
<221> NAME/KEY: misc_feature
<222> LOCATION: (4)..(4)
<223> OTHER INFORMATION: Alpha-aminoisobutyric acid (Aib)

<400> SEQUENCE: 4

Xaa Asn Phe Xaa
1

<210> SEQ ID NO 5
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 5

Gln Lys Leu Val Phe Phe
1               5

<210> SEQ ID NO 6
<211> LENGTH: 2
<212> TYPE: PRT
<213> ORGANISM: Artificial Sequence
<220> FEATURE:
<223> OTHER INFORMATION: Synthetic Peptide

<400> SEQUENCE: 6

Tyr Tyr
1

<210> SEQ ID NO 7
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Stereoisomer D

<400> SEQUENCE: 7

Phe Phe Pro
1

<210> SEQ ID NO 8
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (2)..(3)
<223> OTHER INFORMATION: Stereoisomer D
<220> FEATURE:
<221> NAME/KEY: misc_feature
<222> LOCATION: (4)..(4)
<223> OTHER INFORMATION: Alpha-aminoisobutyric acid (Aib)

<400> SEQUENCE: 8

Xaa Phe Asn Xaa
1
```

```
<210> SEQ ID NO 9
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (4)..(4)
<223> OTHER INFORMATION: Alpha-aminoisobutyric acid (Aib)

<400> SEQUENCE: 9

Xaa Asn Phe Xaa
1

<210> SEQ ID NO 10
<211> LENGTH: 2
<212> TYPE: PRT
<213> ORGANISM: Artificial Sequence
<220> FEATURE:
<223> OTHER INFORMATION: Synthetic Peptide

<400> SEQUENCE: 10

Tyr Tyr
1

<210> SEQ ID NO 11
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: amidated amino acid

<400> SEQUENCE: 11

Tyr Tyr
1

<210> SEQ ID NO 12
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Alpha-aminoisobutyric acid (Aib)

<400> SEQUENCE: 12

Xaa Phe Phe
1

<210> SEQ ID NO 13
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Alpha-aminoisobutyric acid (Aib)
```

```
<400> SEQUENCE: 13

Asn Tyr Xaa
1

<210> SEQ ID NO 14
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 14

Asn Tyr Pro
1

<210> SEQ ID NO 15
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Beta-aminoisobutyric acid
<220> FEATURE:
<221> NAME/KEY: misc_feature
<222> LOCATION: (2)..(4)
<223> OTHER INFORMATION: Stereoisomer D

<400> SEQUENCE: 15

Xaa Pro Tyr Asn
1

<210> SEQ ID NO 16
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Stereoisomer D
<220> FEATURE:
<221> NAME/KEY: misc_feature
<222> LOCATION: (2)..(2)
<223> OTHER INFORMATION: Alpha-aminoisobutyric acid (Aib)

<400> SEQUENCE: 16

Tyr Xaa
1

<210> SEQ ID NO 17
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Stereoisomer D

<400> SEQUENCE: 17

Pro Tyr
1
```

```
<210> SEQ ID NO 18
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Stereoisomer D

<400> SEQUENCE: 18

Tyr Pro
1

<210> SEQ ID NO 19
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 19

Asn Tyr Tyr Pro
1

<210> SEQ ID NO 20
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Alpha-aminoisobutyric acid (Aib)

<400> SEQUENCE: 20

Tyr Tyr Xaa
1

<210> SEQ ID NO 21
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Alpha-aminoisobutyric acid (Aib)

<400> SEQUENCE: 21

Xaa Tyr Tyr
1

<210> SEQ ID NO 22
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (4)..(4)
<223> OTHER INFORMATION: Alpha-aminoisobutyric acid (Aib)
```

```
<400> SEQUENCE: 22

Xaa Tyr Tyr Xaa
1

<210> SEQ ID NO 23
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Stereoisomer D
<220> FEATURE:
<221> NAME/KEY: misc_feature
<222> LOCATION: (4)..(4)
<223> OTHER INFORMATION: Stereoisomer D

<400> SEQUENCE: 23

Asn Tyr Tyr Pro
1

<210> SEQ ID NO 24
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 24

Pro Tyr Tyr
1

<210> SEQ ID NO 25
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 25

Tyr Tyr Pro
1

<210> SEQ ID NO 26
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 26

Pro Tyr Tyr Pro
1

<210> SEQ ID NO 27
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Stereoisomer D
```

<400> SEQUENCE: 27

Tyr Tyr
1

<210> SEQ ID NO 28
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Stereoisomer D
<220> FEATURE:
<221> NAME/KEY: misc_feature
<222> LOCATION: (2)..(2)
<223> OTHER INFORMATION: Alpha-aminoisobutyric acid (Aib)

<400> SEQUENCE: 28

Pro Xaa
1

<210> SEQ ID NO 29
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Stereoisomer D

<400> SEQUENCE: 29

Phe Pro
1

<210> SEQ ID NO 30
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Stereoisomer D
<220> FEATURE:
<221> NAME/KEY: misc_feature
<222> LOCATION: (2)..(2)
<223> OTHER INFORMATION: Alpha-aminoisobutyric acid (Aib)

<400> SEQUENCE: 30

Trp Xaa
1

<210> SEQ ID NO 31
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Stereoisomer D

```
-continued

<400> SEQUENCE: 31

Trp Pro
1

<210> SEQ ID NO 32
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Stereoisomer D

<400> SEQUENCE: 32

Phe Pro
1

<210> SEQ ID NO 33
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Stereoisomer D

<400> SEQUENCE: 33

Pro Phe
1
```